United States Patent [19]
Druliner et al.

[11] Patent Number: 6,121,184
[45] Date of Patent: *Sep. 19, 2000

[54] SUPPORTED BIS(PHOSPHORUS) LIGANDS

[75] Inventors: Joe Douglas Druliner; Kenneth Gene Moloy, both of Newark; Manxue Wang, Wilmington, all of Del.

[73] Assignee: E. I. du Pont de Nemours and Company, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 09/111,942

[22] Filed: Jul. 8, 1998

Related U.S. Application Data

[60] Provisional application No. 60/054,003, Jul. 29, 1997.

[51] Int. Cl.$^7$ .......................... C07C 69/94; C07C 233/64; C07D 319/06
[52] U.S. Cl. .......................... 502/159; 502/164; 502/166; 502/326; 502/402; 502/406; 560/100; 564/180; 549/374
[58] Field of Search ........................ 514/105, 452, 514/623; 549/374; 560/100; 564/180; 502/159, 326, 337, 339, 402, 406, 164, 166

[56] References Cited

U.S. PATENT DOCUMENTS

| | | | |
|---|---|---|---|
| 3,496,215 | 2/1970 | Drinkard et al. | 260/465.8 |
| 3,631,191 | 12/1971 | Kane et al. | 260/439 R |
| 3,655,723 | 4/1972 | Drinkard, Jr. | 260/465.3 |
| 3,766,237 | 10/1973 | Chia et al. | 260/465.3 |
| 4,897,197 | 1/1990 | Williams . | |
| 4,937,292 | 6/1990 | Slemon . | |
| 5,235,113 | 8/1993 | Sato et al. | 568/454 |
| 5,432,289 | 7/1995 | Pugin et al. | 549/221 |
| 5,512,695 | 4/1996 | Kreutzer et al. | 558/338 |
| 5,512,696 | 4/1996 | Kreutzer et al. | 558/338 |

FOREIGN PATENT DOCUMENTS

| | | |
|---|---|---|
| 0 040 891 | 12/1981 | European Pat. Off. . |
| 0 472 071 | 2/1992 | European Pat. Off. . |
| WO 93/03839 | 3/1993 | WIPO ............... C07F 9/46 |
| WO 95/14659 | 6/1995 | WIPO ............ C07C 253/10 |
| WO 96/16022 | 5/1996 | WIPO . |

OTHER PUBLICATIONS

Tolman et al., *Advances in Catalysis*, 33, 1, 1985.
Baker, M.J. et al., *J. Chem. Soc.*, 1292, 1991.
Baker et al., *J. Chem. Soc.*, 803, 1991.
Cuny et al., *J. Am. Chem. Soc.*, 115, 2066, 1993.
Leeuwen et al., Macromol. Symp., 80 (1994) 241–256.
Moroz et al., J. Molecular Catalysis A: Chemical, 112 (1996) 217–233.
Behringer et al., Chem. Commun. (1996) 653–54.
C.C. Leznoff et al., *Canadian Journal of Chemistry*, 51, 3756–3764, 1973.
B. Altava et al., *J. Org. Chem.*, 62, 3126–3134, 1997.
C. U. Pittman Jr. Polymer Supported Catalysts in: Comprehensive Organometallic Chemistry, Pergamon Press, (1982) pp. 553–611.

*Primary Examiner*—Joseph McKane
*Assistant Examiner*—Taofiq A. Solola

[57] ABSTRACT

Supported bis(phosphorus) ligands are disclosed for use in a variety of catalytic processes, including the hydrocyanation of unsaturated organic compounds. Catalysts are formed when the ligands are combined with a catalytically active metal (e.g., nickel).

24 Claims, No Drawings

SUPPORTED BIS(PHOSPHORUS) LIGANDS

This application claims the priority benefit of U.S. Provisional Application No. 60/054,003, filed Jul. 29, 1997.

FIELD OF THE INVENTION

The invention generally relates to supported bis (phosphorus) ligands useful for a variety of catalytic processes. In particular, the ligands are useful in the hydrocyanation of unsaturated organic compounds.

BACKGROUND OF THE INVENTION

Phosphorus ligands are ubiquitous in catalysis, finding use for a number of commercially important chemical transformations. Phosphorus ligands commonly encountered in catalysis include phosphines (A), and phosphites (B), shown below. In these representations R can be virtually any organic group. Monophosphine and monophosphite ligands are compounds which contain a single phosphorus atom which serves as a donor to a metal. Bisphosphine, bisphosphite, and bis(phosphorus) ligands in general, contain two phosphorus donor atoms and normally form cyclic chelate structures with transition metals.

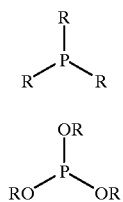

Two industrially important catalytic reactions using phosphorus ligands of particular importance are olefin hydrocyanation and olefin hydroformylation. Phosphite ligands are particularly good ligands for both of these transformations. For example, the hydrocyanation of ethylenically unsaturated compounds using transition metal complexes with monodentate phosphite ligands is well documented in the prior art. See, for example, U.S. Pat. Nos. 3,496,215, 3,631, 191, 3,655,723 and 3,766,237, and Tolman et al., *Advances in Catalysis*, 33, 1, 1985. Bidentate bisphosphite ligands have been shown to be useful in the hydrocyanation of monoolefinic and diolefinic compounds, as well as for the isomerization of non-conjugated 2-alkyl-3-monoalkenenitriles to 3- and/or 4-monoalkene linear nitriles. See, for example, U.S. Pat. Nos. 5,512,695, 5,512, 696 and WO 9514659. Bidentate phosphite ligands have also been shown to be particularly useful ligands in the hydrocyanation of activated ethylenically unsaturated compounds. See, for example, Baker, M. J., and Pringle, P. G., *J. Chem. Soc.*, Chem. Commun., 1292, 1991; Baker et al., *J. Chem. Soc.*, Chem. Commun., 803, 1991; WO 93,03839. Bidentate phosphite ligands are also useful for alkene hydroformylation reactions. For example, U.S. Pat. No. 5,235,113 describes a hydroformylation process in which an organic bidentate ligand containing two phosphorus atoms linked with an organic dihydroxyl bridging group is used in a homogeneous hydroformylation catalyst system also comprising rhodium. This patent describes a process for preparing aldehydes by hydroformylation of alkenically unsaturated organic compounds, for example 1-octene or dimerized butadiene, using the above catalyst system. Also, phosphite ligands have been disclosed with rhodium in the hydroformylation of functionalized ethylenically unsaturated compounds: Cuny et al., *J. Am. Chem. Soc.*, 1993, 115, 2066. These prior art examples demonstrate the utility of bisphosphite ligands in catalysis.

While these prior art systems represent commercially viable catalysts, they do suffer from significant drawbacks. Primarily, the catalyst, consisting of the ligand and the metal, must be separated from the reaction products. Typically this is done by removing the product and catalyst mixture from the reaction zone and performing a separation. Typical separation procedures involve extraction with an immiscible solvent, distillation, and phase separations. In all of these examples some of the catalyst, consisting of the ligand and/or the metal, is lost. For instance, distillation of a volatile product from a non-volatile catalyst results in thermal degradation of the catalyst. Similarly, extraction or phase separation results in some loss of catalyst into the product phase. These ligands and metals are often very expensive and thus it is important to keep such losses to a minimum for a commercially viable process.

One method to solve the problem of catalyst and product separation is to attach the catalyst to an insoluble support. Examples of this approach have been previously described, and general references on this subject can be found in "Supported Metal Complexes", D. Reidel Publishing, 1985, Acta Polymer. 1996, 47, 1, and Comprehensive Organometallic Chemistry, Pergamon Press, 1982, Chapter 55. Specifically, monophosphine and monophosphite ligands attached to solid supports are described in these references and also in *Macromol. Symp.* 1994, 80, 241. Bisphosphine ligands have also been attached to solid supports and used for catalysis, as described in for example U.S. Pat. No. 5,432,289, *J. Mol. Catal.* A 1996, 112, 217, and *J. Chem. Soc.*, Chem. Commun. 1996, 653. The solid support in these prior art examples can be organic, e.g., a polymer resin, or inorganic in nature.

These prior art systems have to date suffered from several drawbacks and have not reached commercial potential. Among the drawbacks noted in the literature are metal leaching and poor reaction rates. In addition, the prior art systems are often not readily amenable to precise control of the ligand coordination properties, e.g., electronics and steric size. What is needed is a supported bis(phosphorus) ligand system which overcomes the problems and deficiencies inherent in the prior art. Other objects and advantages of the present invention will become apparent to those skilled in the art upon reference to the detailed description which hereinafter follows.

SUMMARY OF THE INVENTION

The present invention provides for novel supported diols and chelating bis(phosphorus) ligands covalently bonded to a support. Preferably, the support is an insoluble polymer such as a crosslinked polystyrene resin or other organic polymer resin.

The supported bis(phosphorus) ligand has the structure (2):

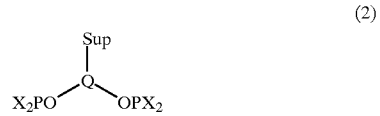

wherein:

Q is any organic fragment which binds a $OPX_2$ moiety to the support (Sup); and X is an alkoxide, aryloxide, alkyl, or aryl.

Preferably, X is aryloxide or aryl.

The invention also provides for a supported catalyst composition having the structure (3):

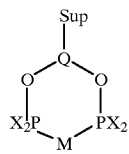
(3)

wherein:

Q is any organic fragment which binds a $OPX_2$ moiety to the support (Sup).;

X is an alkoxide, aryloxide, alkyl or aryl; and

M is a transition metal capable of carrying out catalytic transformations.

X is preferably aryloxide or aryl and M is preferably Ni, Rh, Co, Ir, Pd, Pt or Ru.

The invention also provides for a catalytic process utilizing the above-described supported catalyst compositions. Such processes include, inter alia, hydrocyanation, isomerization, hydrogenation and hydrosilation.

In particular, the invention provides for a hydrocyanation process comprising reacting an acyclic, aliphatic, monoethylenically unsaturated compound in which the ethylenic double bond is not conjugated to any other olefinic group in the molecule, or a monoethylenically unsaturated compound in which the ethylenic double bond is conjugated to an organic ester group, with a source of HCN in the presence of a supported catalyst composition according to formula (3):

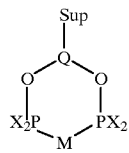
(3)

wherein:

Q is any organic fragment which binds a $OPX_2$ moiety to the support (Sup).;

X is an alkoxide, aryloxide, alkyl or aryl; and

M is nickel.

The invention further provides for the hydrocyanation of diolefinic compounds comprising reacting an acyclic aliphatic diolefinic compound with a source of HCN in the presence of a supported catalyst composition according to formula (3):

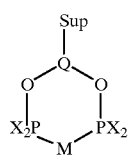
(3)

wherein:

Q is any organic fragment which binds a $OPX_2$ moiety to the support (Sup).;

X is an alkoxide, aryloxide, alkyl or aryl; and

M is nickel.

This process may be run in either the liquid or vapor phase.

DETAILED DESCRIPTION OF THE PREFERRED EMBODIMENTS

A primary aim of this invention is to provide catalysts for a number of industrially important reactions characterized by the fact that these catalysts are covalently attached to an insoluble support. These catalysts are additionally characterized by the fact that they consist of a chelating ligand covalently attached to an insoluble support. The chelate ligand coordinates catalytically active transition metals. The advantages of this process are:

These catalysts are insoluble and non-volatile, allowing ready separation from the reaction medium by filtration or other means, or use in fixed bed, flow-through reactors using either liquid or gas phase carrier streams.

The chelating arrangement of donor atoms gives catalysts with commercially practical activity and selectivity. In particular, the chelates described herein are based on bisphosphite ligands, in which it is known that soluble derivatives give catalysts with significantly improved reaction rates and selectivities over monophosphite ligands.

The chelating arrangement of donor atoms results in a much stronger ligand-metal interaction and thus greatly minimizes the potential for metal leaching.

It is possible to methodically alter the spacing between the chelating atoms, the steric environment of these atoms, and the electronic properties of the donor atoms, thereby offering precise control of ligand coordination properties; this in turn allows significant opportunity to optimize catalyst performance.

The chemical environment in the immediate vicinity of the catalytically active site is uniform throughout the solid support matrix. The catalyst therefore acts as a "single site" type of catalyst, as opposed to an ensemble of different catalysts.

The supported bis(phosphorus) ligands described herein may be used as a component of a catalyst system for a number of catalytic processes, e.g., hydrocyanation, hydrogenation, hydroformylation, polymerization, isomerization, hydrosilation, carbonylation, cross-coupling, and metathesis. The supported bis(phosphorus) ligands described herein generally form the catalyst when combined with a catalytically active metal. The resulting supported catalyst forms a separate phase from the reaction medium, reacting substrates, and products. The reaction medium may be composed of a liquid solvent which does not interfere with the catalytic reaction of interest, or may be gaseous, e.g., an inert carrier gas and gaseous reactants and products.

It has been found that the supported bis(phosphorus) ligands of the present invention are particularly suitable for use in the hydrocyanation of unsaturated organic compounds in combination with a transition metal compound, the metal of which is for example nickel, platinum, palladium, or cobalt. Of the transition metals useful for hydrocyanation, nickel is especially preferred. The polymer-supported bis (phosphorus) ligands of the present invention are also suitable for use in the hydrogenation and hydrosilation of double bonds in combination with a transition metal. Rhodium is especially preferred for phosphine-promoted hydrogenation and hydrosilation.

DESCRIPTION OF THE SUPPORT

Virtually any solid material may be used as a support in the context of this invention as long as it meets the following criteria:

The material is insoluble in organic, aqueous, or inorganic solvents. Organic polymer supports are acceptable in this regard but they generally need to be crosslinked. Inorganic supports, such as metal oxides (silicas, etc.) are generally insoluble in these solvents and also may be used as supports.

The support contains reactive sites which can be used for the covalent attachment of organic fragments containing a diol group (as described below) or a protected diol group.

The reactive sites are isolated to prevent additional crosslinking during further chemical transformations.

The reactive sites are exposed to the reaction medium. With a polymer resin support this is achieved through the use of resins which swell in a reaction solvent or is sufficiently porous to allow transport of the reaction medium through the polymer matrix.

The term "solid support" or "support" (sup) refers to a material having a rigid or semi-rigid surface which contain or can be derivatized to contain functionality which covalently links a compound to the surface thereof. Such materials are well known in the art and include, by way of example, polystyrene supports, polyacrylamide supports, polyethyleneglycol supports, and the like. Such supports will preferably take the form of small beads, pellets, disks, or other conventional forms, although other forms may be used.

The supports described in this application are functionalized poly(styrene) resins. Other suitable polymers include polyolefins, polyacrylates, polymethacrylates, and copolymers thereof that meet the general criteria described above. Specifically, poly(styrene) resins commonly used for solid phase synthesis have been used. These particular resins are crosslinked with from 1 to 10 wt % divinylbenzene. The styrene moieties are substituted in the para or meta positions. Only a portion of the styrene moieties are substituted, typically resulting in functional group loadings of approximately 0.2 to 2.0 mmole per gram of resin, although this value may be higher or lower.

DESCRIPTION AND PREPARATION OF SUPPORTED DIOLS

The aims of this invention are achieved by construction of a chelating ligand covalently bonded to an insoluble support (Sup), preferably a polymer support (Pol). The first step of this procedure involves the preparation of a diol group covalently attached to an insoluble support as exemplified by the following structure:

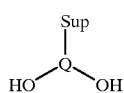

(1)

wherein, Sup represents the insoluble support. As used herein, Q means any organic fragment which binds the diol moiety to the support. For example, Q may consist of from 2 to 50 carbon atoms, in addition to heteroatoms such as nitrogen, oxygen, and the like. Q may additionally contain functional groups such as ether, acetal, ketal, ester, amide, amine, imine, etc., and combinations thereof. Q may also contain saturated or unsaturated carbon-carbon bonds. Q may or may not be symmetrical.

The number of atoms present in Q and used to separate the two OH moieties of the diol is generally limited to between 2 and 10, although any number and arrangement which ultimately allows the formation of a chelating ring is acceptable. A preferred number is 2 to 5 atoms. These atoms may be carbon or heteroatoms such as oxygen and nitrogen. The atoms may further comprise a chain or cyclic structure, the latter of which may be saturated or unsaturated, e. g., aromatic.

The preparation of materials of Formula 1 follows methods known to those skilled in the art. The procedure may involve one reaction step or multiple reaction steps. Preferred methods are those which proceed in high yield, high selectivity, are inexpensive, and are simple to conduct. For example, Can. J. Chem. 1973, 51, 3756, describes the synthesis of the material of formula SD6. The synthesis occurs in two reaction steps from inexpensive materials and in high yield. Other materials described in this invention have not been previously reported in the literature but follow reaction steps known for soluble, non-polymer supported analogues. For instance, reaction of the polymer-supported benzaldehyde pol-CHO, prepared by the method described in J. Polym. Sci.1975, 13, 1951 and J. Polym. Sci., Polym. Lett. 1965, 3, 505, with pentaerythritol gives polymer-supported diol SD1. The analogous reaction of soluble, non-polymer supported benzaldehyde with pentaerythritol is described in Org. Syn. Vol 38, 65. Alternatively, reaction of polymer-supported aldehyde pol-CHO with diethyl tartrate, followed by reduction, leads to the class of polymer-supported diols SD2, 3, 4. SD3 is described in J. Org. Chem., 1997, 62, 3126. The analogous reactions of the soluble, non-polymer supported compounds are described in Helv. Chim. Acta 1983, 66, 2308 and J. Org. Chem. 1993, 58, 6182. Supported alkylene-bridged bisaryl alcohols can be prepared by methods found in J. Chem. Soc., Perkin I, 1980, 1978–1985; Indian J. Chem. 1995, 34B, 6–11, and Chem. Ber. 1985,118, 3588–3619. Other examples may be prepared by known organic transformations, and representative structures are shown below.

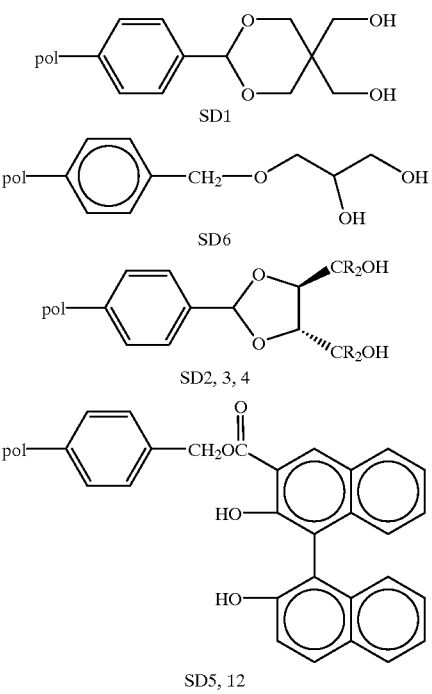

-continued

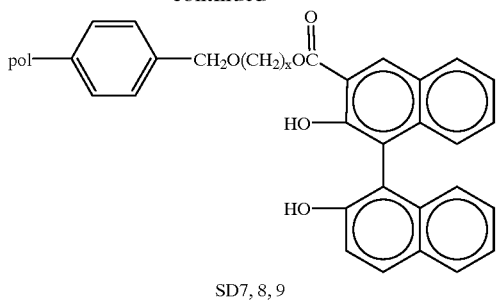

SD7, 8, 9

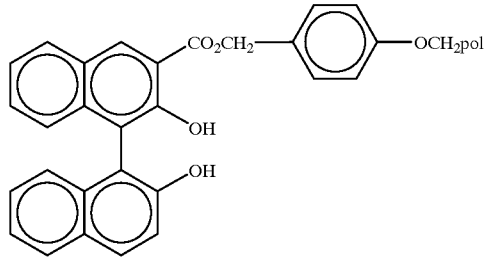

SD11

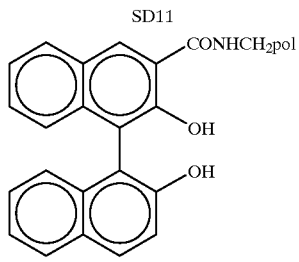

SD10

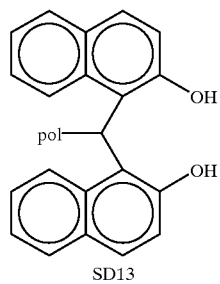

SD13

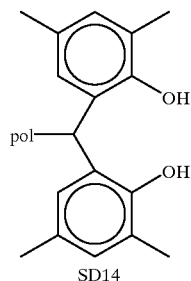

SD14

DESCRIPTION AND PREPARATION OF POLYMER-SUPPORTED BIS(PHOSPHORUS) LIGANDS

The polymer-supported bis(phosphorus) ligands may be prepared by a variety of methods known in the art, for example, see descriptions in WO 93,03839; U.S. Pat. Nos. 4,769,498 and 4,668,651. In general, the transformation involves the reaction of a phosphorus halide, typically but not limited to chloride, with the diol to form P-O bonds. The phosphorus halide may be any compound of the type $PY_n$ $X_{3-n}$, where Y=halide, X=alkoxide, aryloxide, alkyl, aryl, and n=3, 2, or 1. The phosphorus halides most useful for the present invention are those where Y=Cl; X=alkoxide, aryloxide, alkyl, or aryl; and n=1. The group X may contain from 1 to 50 carbon atoms. It may also optionally contain heteroatoms such as oxygen, nitrogen, halogen, and the like, and also functional groups such as ethers, alcohols, esters, amides, as well as others. The groups X may or may not be linked to form a cyclic structure. The $PX_2$ moiety may form a ring and $X_2$ may be a di(alkoxide), di(aryloxide), di(alkyl) or di(aryl). Many dialkylchlorophosphines and diarylchlorophosphines are commercially available, or may be prepared by methods known in the art, for example, *J. Am. Chem. Soc.* 1994, 116, 9869. Phosphorochloridites, may be prepared by a variety of methods known in the art, for example, see descriptions in *Polymer* 1992, 33, 161; *Inorg. Syn.* 1966, 8, 68; U.S. Pat. No. 5,210,260; *Z. Anorg. Allg. Chem.* 1986, 535, 221. For example, the reaction of 2,2'-biphenol with phosphorus trichloride gives 1,1'-2,2'-diylphosphorochloridite.

The reaction of these chlorophosphorus reagents with a material of Formula 1 in the presence of a base gives a polymer-supported bis(phosphorus) ligand exemplified by the structure shown:

$$X_2PO \underset{Q}{\overset{Pol}{\diagup}} OPX_2 \qquad (2)$$

where X and Q are as defined above. Other examples may be prepared by similar transformations, and representative structures are also shown below.

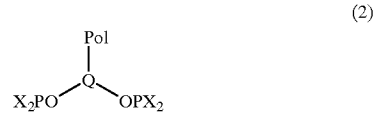

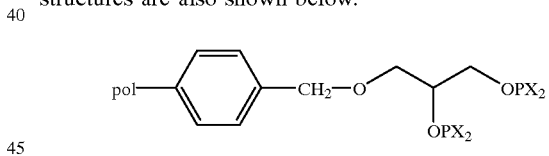

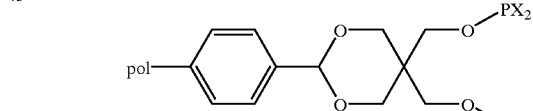

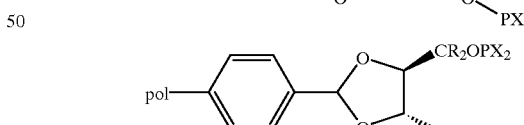

R = H, CH₃

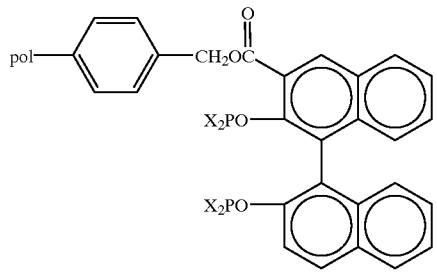

-continued

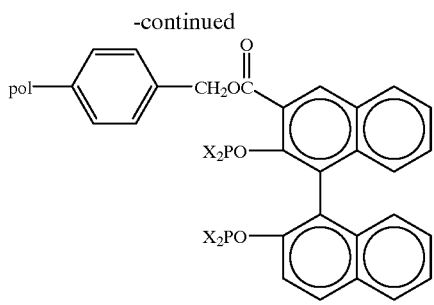

DESCRIPTION AND PREPARATION OF POLYMER-SUPPORTED TRANSITION METAL CATALYSTS

The transition metal catalysts which are a subject of this invention are defined by the formula shown below:

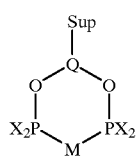

(3)

wherein Q and X are as defined above. M is a transition metal capable of carrying out catalytic transformations. M may additionally contain labile ligands which are either displaced during the catalytic reaction, or take an active part in the catalytic transformation. Any of the transition metals may be considered in this regard. The preferred metals are those comprising groups 8, 9, and 10 of the Periodic Table. The catalytic transformations possible with these catalysts comprise, but are not limited to, hydrocyanation, hydroformylation, hydrogenation, hydrosilation, cross-coupling, isomerization, carbonylation, and metathesis. The most preferred metal for hydrocyanation is nickel, and the preferred metals for hydrosilation, hydrogenation, and hydroformylation are rhodium, cobalt, iridium, palladium and platinum, the most preferred being rhodium.

The zero-valent nickel compounds, suitable for hydrocyanation, can be prepared or generated according to techniques well known in the art, as described, for example, U.S. Pat. Nos. 3,496,217; 3,631,191; 3,846,461; 3,847,959; and 3,903,120. Zero-valent nickel compounds that contain ligands which can be displaced by the organophosporus ligands are a preferred source of zero-valent nickel. Two such preferred zero-valent nickel compounds are $Ni(COD)_2$ (COD is 1,5-cyclooctadiene) and $Ni\{P(O\text{-}o\text{-}C_6H_4CH_3)_3\}_2$ $(C_2H_4)$, both of which are known in the art. Alternatively, divalent nickel compounds may be combined with a reducing agent, to serve as a source of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Li, Na, K, or $H_2$.

Rhodium catalysts suitable for hydrogenation and hydrosilation can be prepared by techniques well known in the art as described, for example, in *J. Amer. Chem. Soc.* 1976, 98, 2134, *J. Org. Chem.* 1977, 42, 1671, and *J. Amer. Chem. Soc.* 1973, 95, 8295. For example, monovalent rhodium compounds that contain ligands which can be displaced by the supported organophosphorus ligands are a preferred source of monovalent rhodium. Examples of such preferred monovalent rhodium compounds are $Rh(COD)_2X$ (where COD is as defined above and X is negatively charged counterion such as halide, $BF_4^-$, $PF_6^-$, OTf (OTf= $O_3SCF_3$), $ClO_4^-$, and the like), $Rh(PPh_3)_3Cl$, and $Rh(CO)_2$ (acac) (acac=acetylacetonate).

DESCRIPTION OF CATALYTIC PROCESSES— HYDROCYANATION OF DIOLEFINIC COMPOUNDS

The diolefinic compound reactants used in this study include primarily conjugated diolefins containing from 4 to 10 carbon atoms; for example, 1,3-butadiene and cis and trans-2,4-hexadienes. Butadiene is especially preferred by reason of its commercial importance in the production of adiponitrile. Other suitable diolefinic compounds include diolefinic compounds substituted with groups which do not deactivate the catalyst, for example, cis and trans-1,3-pentadienes.

The following Formulas†I and II illustrate suitable representative starting diolefinic compounds; and Formulas III, IV, and V represent the products obtained from 1,3-butadiene and HCN.

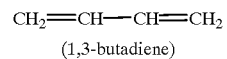

(1,3-butadiene)

I

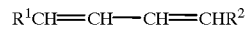

II wherein each one of $R^1$ and $R^2$, independently, is H or a $C_1$ to $C_3$ alkyl.

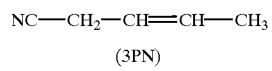

(3PN)

III

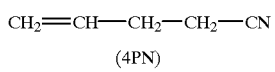

(4PN)

IV

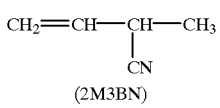

(2M3BN)

V

It will be recognized that Compound I is a special case of Formula II, where each one of $R^1$ and $R^2$ is hydrogen.

The hydrocyanation reaction can be carried out with or without a solvent. The solvent should be a liquid at room temperature and inert towards the unsaturated compound and the catalyst. Generally, such solvent are hydrocarbons such as benzene, xylene, or nitriles such as acetonitrile, benzonitrile or adiponitrile. The reaction may also be carried out with the reactants and products present in the gas phase.

The exact temperature used is dependent, to a certain extent, on the particular catalyst being used, the particular unsaturated compound being used, the volatility of the reactants and products, and the desired rate. Generally, temperatures of from −25° C. to 200° C., can be used with from 0° C. to 175° C. being the preferred range.

The mole ratio of unsaturated compound to catalyst generally is varied from about 10:1 to 100,000 to:1, preferably 100:1 to 5,000:1, unsaturated compound to catalyst for a batch operation. In a continuous operation such as when using a fixed bed catalyst type of operation, a higher proportion of catalyst may be used such as 5:1 to 100,000:1, preferably 100:1 to 5,000:1, unsaturated compound to catalyst.

Preferably, when a liquid reaction medium is used, the reaction mixture is agitated, such as by stirring or shaking.

The cyanated product can be recovered by conventional techniques such as crystallization of the product from the solution or by distillation.

One can either isolate the 2-alkyl-3-monoalkenenitriles produced by the hydrocyanation of the diolefin or proceed continuously with the isomerization under similar reaction conditions.

The hydrocyanation process may also be conducted in the vapor phase wherein an acyclic aliphatic diolefinic compound, preferably butadiene, is reacted with HCN in the vapor phase. This process is similar to that described in U.S. Pat. Nos. 5,449,807 and 5,440,067 (both to Druliner) and U.S. Provisional Application No. 60/014,618, filed Apr. 2, 1996, with the exception that the catalyst employed is the same as that described in this invention. The temperature of such a gas phase process can vary from about 135° C. to about 170° C.

The supported nickel catalysts of formula 3 (M=Ni(0)) are loaded into tubular reactors, and a gaseous diolefinic compound, e.g., butadiene, and HCN is passed continuously over the solid catalysts at temperatures sufficiently high to maintain the starting materials as well as the reaction products in the vapor phase. The temperature range is generally from about 135° C. to about 300° C. and preferably from about 145° C. to 200° C. The temperature must be high enough to maintain all of the reactants and products in the vapor phase but low enough to prevent deterioration of the catalyst. The particular preferred temperature depends to some extent on the catalyst being used, the diolefinic compound being used, and the desired reaction rate. The operating pressure is not particularly critical and can conveniently be from about 1–10 atmospheres (101.3 to 1013 kPa). No practical benefit is obtained when operating above the upper limit of this pressure range.

HCN and/or the diolefinic starting materials can be delivered as a neat vapor or as a preheated solution in a solvent, such as acetonitrile or toluene. Under atmospheric pressure, using nitrogen or other inert gas as carrier, temperatures of from about 140–160° C. are typically used. Nitrogen is preferred because of its low cost. Gaseous oxygen, water vapor, or other gaseous substance which could react with HCN, the catalyst, or the starting diolefinic compound should be avoided. The reaction products are liquid at room temperature and are conveniently recovered by cooling. Branched 2-methyl-3-butenenitrile can be separated from linear 3- and 4-pentenenitrile by distillation.

DESCRIPTION OF CATALYTIC PROCESSES— HYDROCYANATION OF MONOOLEFINIC COMPOUNDS

The present invention also provides a process for hydrocyanation, comprising reacting a nonconjugated, acyclic, aliphatic, monoethylenically unsaturated compound or 2-pentenenitrile or an alkyl-2-pentenoate with a source of HCN in the presence of a Lewis acid promoter catalyst composition formed by the supported nickel catalysts described previously and depicted by Formula 3.

Representative ethylenically unsaturated compounds which are useful in the process of this invention are shown in Formula VI or VIII, and the corresponding terminal nitrile compounds produced are illustrated by Formula VII or IX, respectively, wherein like reference characters have same meaning.

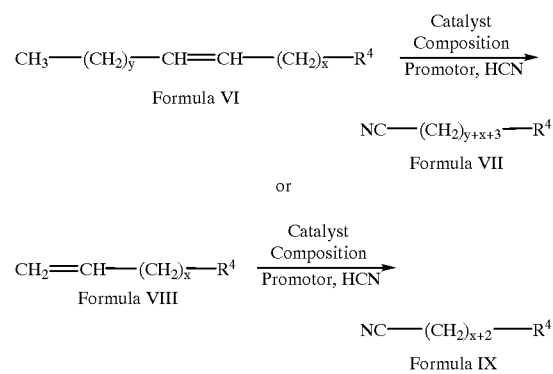

wherein
$R^4$ is H, CN, $CO_2R^5$, or perfluoroalkyl;
y is an integer of 0 to 12;
x is an integer of 0 to 12 when $R^4$ is H, $CO_2R^5$ or perfluoroalkyl;
x is an integer of 1 to 12 when $R^4$ is CN; and
$R^5$ is alkyl.

The nonconjugated acyclic, aliphatic, monoolefinically unsaturated starting materials useful in this invention include unsaturated organic compounds containing from 2 to approximately 30 carbon atoms. The 3-pentenenitrile and 4-pentenenitrile are especially preferred. As a practical matter, when the nonconjugated acyclic aliphatic monoethylenically unsaturated compounds are used in accordance with this invention, up to about 10% by weight of the monoethylenically unsaturated compound may be present in the form of a conjugated isomer, which itself may undergo hydrocyanation. For example, when 3-pentenenitrile is used, as much as 10% by weight thereof may be 2-pentenenitrile. As used herein, the term "pentenenitrile" is intended to be identical with "cyanobutene". Suitable unsaturated compounds include unsubstituted hydrocarbons as well as hydrocarbons substituted with groups which do not attack the catalyst, such as cyano. These unsaturated compounds include monoethylenically unsaturated compounds containing from 2 to 30 carbons such as ethylene, propylene, butene-1, pentene-2, hexene-2, etc.; nonconjugated diethylenically unsaturated compounds such as allene; and substituted compounds such as 3-pentenenitrile, 4-pentenenitrile, methyl pent-3-enoate; and ethylenically unsaturated compounds having perfluoroalkyl substituents such as, for example, $C_zF_{2z+1}$, where z is an integer of up to 20. The monoethylenically unsaturated compounds may also be conjugated to an ester group such as methyl pent-2-enoate.

The starting olefinically unsaturated compounds useful in this invention and the hydrocyanation products thereof are those shown above in Formulas VI through VIII. Those of Formula VI yield terminal nitrites of Formula VII, while those of Formula VIII yield terminal nitrites of Formula IX.

Preferred are nonconjugated linear alkenes, nonconjugated linear alkenenitriles, nonconjugated linear alkenoates, linear alk-2-enoates and perfluoroalkyl ethylenes. Most preferred substrates include 3- and 4-pentenenitrile, alkyl 2-, 3-, and 4-pentenoates, and $C_zF_{2z+1}CH=CH_2$ (where z is 1 to 12).

The preferred products are terminal alkanenitriles, linear dicyanoalkylenes, linear aliphatic cyanoesters, and 3-(perfluoroalkyl)propionitrile. Most preferred products are adiponitrile, alkyl 5-cyanovalerate, and $C_zF_{2z+1}CH_2CH_2CN$, where z is 1 to 12.

The hydrocyanation of monoolefinic compounds may be carried out by charging a reactor with all of the reactants, or preferably on a commercial scale, the reactor is charged with the catalyst components, the unsaturated organic compound, the promoter, and the solvent to be used, and the hydrogen cyanide is added slowly. HCN may be delivered as a liquid or as a vapor to the reaction. Another technique is to charge the reactor with the catalyst, promoter, and the solvent to be used, and to feed both the unsaturated organic compound and the HCN slowly to the reaction mixture. The molar ratio of unsaturated monoolefinic compound to catalyst is generally varied from about 10:1 to 2000:1. The molar ratio of phosphorus compound to nickel is in the range 0.5:1 to 20:1.

Preferably, the reaction medium is agitated, such as by stirring or shaking. The cyanated product can be recovered by conventional techniques, such as by distillation. The reaction may be run batchwise or in a continuous manner.

The hydrocyanation reaction can be carried out with or without a solvent. The solvent, if used, should be liquid at the reaction temperature and pressure and inert towards the unsaturated compound and to the catalyst. Suitable such solvents include hydrocarbons such as benzene or xylene and nitriles such as acetonitrile or benzonitrile. In some cases, the unsaturated compound to be hydrocyanated may itself serve as the solvent.

The exact temperature is dependent to a certain extent on the particular catalyst being used, the particular unsaturated compound being used and the desired rate. Normally, temperatures of from −25° C. to 200° C. can be used, the range of 0° C. to 150° C. being preferred.

Atmospheric pressure is satisfactory for carrying out the present invention and hence pressure of from about 0.05 to 10 atmospheres (50.6 to 1013 kPa) are preferred. Higher pressures, up to 10,000 kPa or more, can be used, if desired, but any benefit that may be obtained thereby would not justify the increased cost of such operations.

HCN can be introduced to the reaction as a vapor or liquid. As an alternative, a cyanohydrin can be used as the source of HCN. See, for example, U.S. Pat. No. 3,655,723.

The process of this invention is carried out in the presence of one or more Lewis acid promoters which affect both the activity and the selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_2$, $FeCl_3$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $Ph_2AlCl$, $Ph_2AlCl$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $BPh_3$, $TaCl_5$. Suitable promoters are further described in U.S. Pat. Nos. 3,496,217; 3,496,218,; 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters are $CdCl_2$, $ZnCl_2$, $B(C_6H_5)_3$, and $(C_6H_5)_3 SnX$, where $X=CF_3SO_3$, $CH_3C_6H_5SO_3$, or $(C_6H_5)_3BCN$. The mole ratio of promoter to nickel present in the reaction can be within the range of 1:16 to 50: 1.

DESCRIPTION OF CATALYTIC PROCESSES—HYDROGENATION

Olefinic compounds of the type shown below are converted to the corresponding saturated alkane by the catalysts of the title invention.

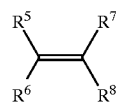

(4)

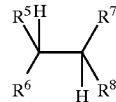

(5)

$R^5$, $R^6$, $R^7$, and $R^8$ represent hydrogen or hydrocarbyl groups of up to 20 carbon atoms. $R^5$, $R^6$, $R^7$, and $R^8$ may be aromatic or saturated, and may be the same or different.

The hydrogenation process may be carried out at a temperature of from about room temperature, e.g., 20° C., to about 150° C. A preferable range is from about 30° C. to about 100° C. The hydrogen pressure may be varied from about 15 psia to 2000 psia. A preferred range is from about 15 psia to about 300 psia. The reaction time can vary and normally depends on the temperature and pressure.

Generally, with the preferred temperatures and pressures, the reactions are complete within 1–10hours. Rhodium is the preferred metal for hydrogenation of carbon-carbon double bonds, but ruthenium, platinum, and palladium may also be used. The ratio of substrate to catalyst dependes primarily on the reactor configuration but can range from about 50:1 to 50,000:1.

DESCRIPTION OF CATALYTIC PROCESSES—HYDROSILATION

Unsaturated compounds can be converted to silanes with the catalysts of the title invention. Ketones, alkenes, and alkynes may be converted to silanes, as shown in the Scheme below. Scheme:

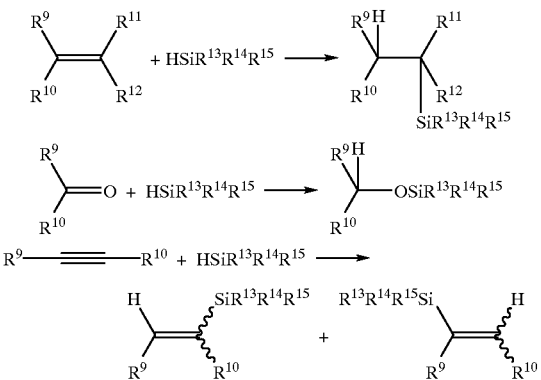

$R^9$, $R^{10}$, $R^{11}$, and $R^{12}$ represent hydrogen or hydrocarbyl groups of up to 20 carbon atoms. $R^9$, $R^{10}$, $R^{11}$, and $R^{12}$ may be aromatic or saturated, and may be the same or different. $R^{13}$, $R^{14}$, and $R^{15}$ represent hydrogen, hydrocarbyl, or alkoxy groups of up to 20 atoms. $R^{13}$, $R^{14}$ and $R^{15}$ may be aromatic or saturated, and may be the same or different.

The hydrosilation process may be carried out at from about 0° C. to about 150° C., and a preferable range is from about 20° C. to 100° C. The ratio of substrate to olefin can range from about 1:10 to about 10:1, and a preferred range is from about 1:2 to 2:1. Rhodium is the preferred metal for the phosphine-promoted hydrosilation of double bonds, but ruthenium, platinum, and palladium may also be used. The ratio of substrate to catalyst depends primarily on the reactor configuration but can range from about 50:1 to 50,000:1.

EXAMPLES

The following non-limiting examples further illustrate the invention. All percentages are by weight, unless otherwise noted.

Example 1

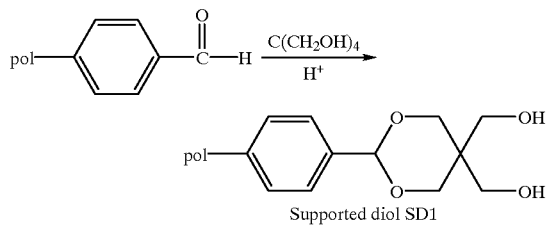

Supported diol SD1

10.2 g of pentaerythritol was dissolved in the minimum amount of dimethyl sulfoxide, and then toluene was added until the solution became slightly cloudy. 18.9 g of the polymer-supported benzaldehyde resin (prepared by oxidation of Merrifield's resin commercially available from Aldrich Chemical Co., Milwaukee, Wis., or Polymer Laboratories, Ltd., Shropshire, England) and a few crystals of p-toluenesulfonic acid were then added. The suspension was brought to reflux and the condensate was passed through a bed of molecular sieves in a Soxhlet extractor before returning to the reaction flask. After 12 h the suspension was cooled to room temperature and the resin was isolated by filtration. After washing with warm 0.5% aq $NaHCO_3$, MeOH, and then hexane the resin was dried under vacuum.

IR: O—H at 3400 $cm^{-1}$; complete loss of C=O at 1701 $cm^{-1}$.

MAS $^{13}C\{^1H\}$ NMR ($CDCl_3$): δ102.7 (acetal carbon); 70.7 (ring O$\underline{C}H_2$); 65.3, 63.7 (axial, equatorial $\underline{C}H_2OH$); 39.6 (quaternary carbon), in addition to polymer backbone and ring resonances.

Example 2

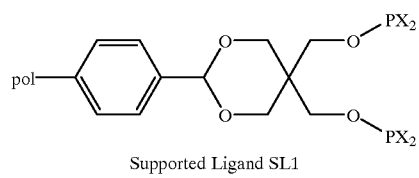

Supported Ligand SL1

$PX_2 = PPh_2$ 1.0 g of resin-supported diol SD1 was suspended in 15 mL pyridine. 0.97 g $PPh_2Cl$ was added dropwise with stirring. After 2.5 days the resin was filtered, washed with 5×10 mL pentane and then dried under vacuum.

MAS $^{13}C\{^1H\}$ NMR ($CDCl_3$): δ102.7 (acetal carbon); 70.3 (ring O$\underline{C}H_2$); 70.0, 68.3 (axial, equatorial $\underline{C}H_2OP$), in addition to polymer backbone and ring resonances.

MAS $^{31}P\{^1H\}$ NMR ($CDCl_3$): 114, 116 ppm.

Example 3

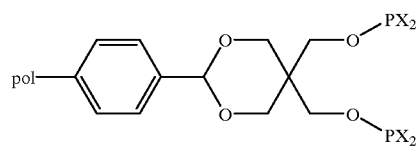

Supported Ligand SL2

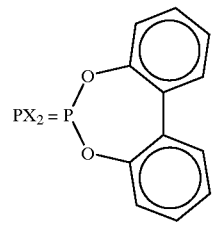

In a manner similar to Example 2, 2.0 g of SD1 was suspended in 15 mL pyridine. 4.4 g of 1,1'-biphenyl-2,2'-diylphosphorochloridite (50 wt % solution in toluene) was added dropwise. The resulting slurry was stirred overnight. The resin was filtered, washed with 2×15 mL of 50/50% $CH_2Cl_2$/pentane, then 3×15 mL pentane, and then dried under vacuum.

Example 4

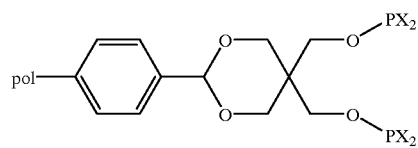

Supported Ligand SL3-1

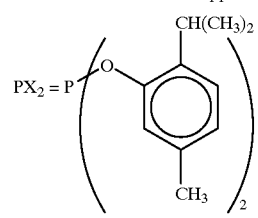

In a manner similar to Example 2, 2.0 g of SD1 was suspended in 15 mL pyridine, and 44 mL of a 0.2 M solution of bis(2-isopropyl-5-methylphenyl)phosphorochloridite in toluene was added dropwise. After stirring overnight the resin was filtered, washed with 3×10 mL 50/50 pyridine/pentane, then 2×10 mL pentane, and finally dried under vacuum.

An identical experiment was performed using a 2% divinylbenzene cross-linked resin support to give supported ligand SL3-2.

$^{31}P\{1H\}$ ($CDCl_3$): 134 ppm.

Example 5

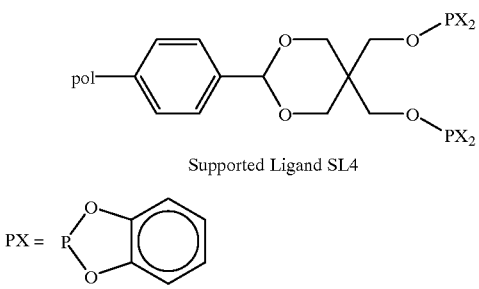

Supported Ligand SL4

In a manner similar to Example 2, 4.20 g of SD1 was suspended in 20 mL pyridine. 1.616 g 1,2-phenylenephosphorochlodite was added dropwise at room temperature. The mixture was then stirred for three days at room temperature and the resulting resin isolated by filtration. After washing thoroughly with pyridine and pentane it was dried under vacuum.

IR: Loss of O—H band at 3400 cm$^{-1}$.

Example 6

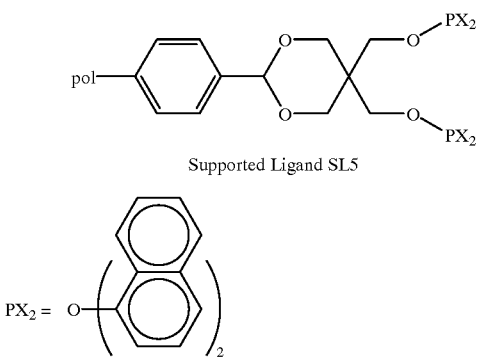

Supported Ligand SL5

In a manner similar to Example 2, 0.98 g of SD1 was suspended in 15 mL of pyridine and then 1.1 g of bis(1-naphthyl)phosphorochloridite was added. The resulting mixture was agitated overnight at room temperature. The product was collected by filtration and then washed with CH$_2$Cl$_2$, THF (tetrahydrofuran), and pentane before vacuum drying.

IR (KBr, cm$^{-1}$): loss of O—H at 3400 cm$^{-1}$.

Elemental analysis: 81.63% C, 6.98% H, 2.78% P.

Example 7

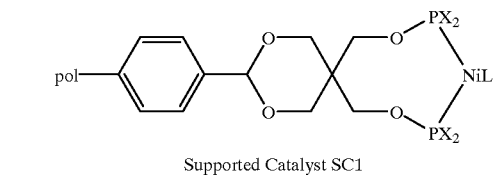

Supported Catalyst SC1

L = 1,5-cyclooctadiene, (CO)2
PX$_2$ = PPh$_2$ 1.53 g of the supported bis(phosphinite) resin SL1 was suspended in 20 mL toluene. A solution of 0.426 g Ni(COD)$_2$ in 10 mL toluene was added, whereupon the mixture turned orange. After 3 h the slurry was filtered to give an orange Ni(COD)-loaded resin which was washed (5×15 mL toluene, 2×15 mL pentane) and dried under vacuum.

0.10 g of the resulting Ni(COD)-supported resin was suspended in 8 mL toluene. The slurry was then treated with CO (1 atm). After 3 h the color changed to a light yellow. The Ni(CO)$_2$-loaded resin was filtered and GC/MS analysis of the filtrate showed the presence of 1,5-cyclooctadiene. The resin was washed with toluene, then pentane, and then vacuum dried.

IR (cm$^{-1}$, KBr): 2013, 1956.

Example 8

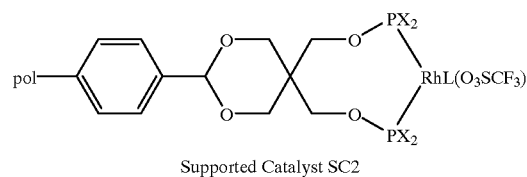

Supported Catalyst SC2

L = 1,5-cyclooctadiene, CO
PX$_2$ = PPh$_2$ 3.0 g of the bis(phosphinite) resin SL1 was suspended in 60 mL of THF. 1.03 g of Rh(COD)$_2$(O$_3$SCF$_3$) was added. The mixture was shaken overnight at room temperature. GC analysis of the supernatant showed the presence of COD. The now orange Rh(COD)(O$_3$SCF$_3$)-loaded resin was isolated by filtration, washed with 2×20 mL of THF and then vacuum dried. Yield=3.275 g.

Analysis: P, 0.83 wt %; Rh, 1.91 wt %.

A small amount of the resulting Rh(COD)(O$_3$SCF$_3$)-loaded resin was suspended in THF and treated with 1 atm CO. GC analysis of the supernatant after 30 min showed the presence of COD. The product was isolated by filtration and dried under vacuum. IR (KBr) showed a strong carbonyl absorption at 2002 cm$^{-1}$ indicative of the supported rhodium carbonyl complex.

Example 9

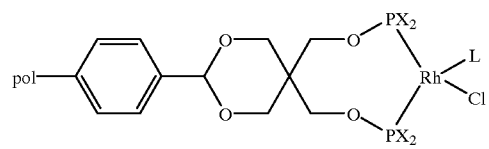

Supported Catalyst SC3

L = PPh$_3$, CO
PX$_2$ = PPh$_2$ 0.50 g of the bis(phosphinite) resin SL1 and 0.34 g of Rh(PPh$_3$)$_3$Cl were weighed into a vial; 20 mL of THF was then added. The suspension was shaken overnight at room temperature. The burgundy solution was filtered to yield an orange solid. The solid was washed with THF until the washings were colorless, and then dried under vacuum. Yield=0.452 g of the orange chlororhodiumtriphenylphosphine loaded resin (L=PPh$_3$), catalyst SC3.

The catalyst was characterized as the rhodium-carbonyl derivative by infrared spectroscopy: 40 mg of the resulting chlororhodiumtriphenylphosphine-loaded resin was suspended in THF and treated with 1 atm of CO at room temperature. After 30 min the orange resin was filtered, washed with THF and dried under vacuum. IR showed a strong absorption at 1981 cm$^{-1}$, consistent with formation of the chlororhodiumcarbonyl loaded resin (L=CO).

Example 10

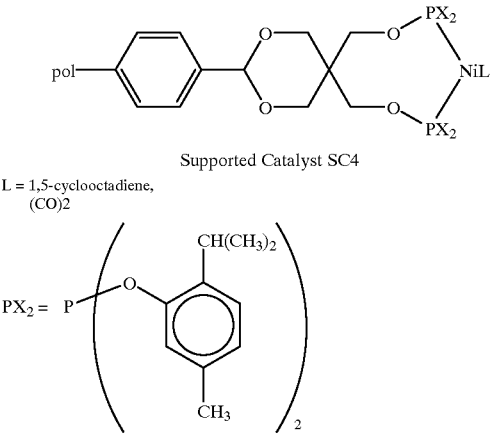

Supported Catalyst SC4

L = 1,5-cyclooctadiene, (CO)2

The resin-supported bis(phosphite) SL3 (1.048 g) was suspended in 15 mL toluene and a solution of 0.243 g Ni(COD)$_2$ was added. The mixture was stirred at room temperature for 2 h. The resulting dark Ni(COD)-loaded resin was isolated by filtration, washed with toluene and pentane, and then dried under vacuum.

100 mg of the resulting Ni(COD)-loaded resin was suspended in toluene and treated with 1 atm CO. After 3 h the resin was filtered, washed with toluene and hexane, and then vacuum dried. GC/MS analysis showed liberation of COD. IR showed carbonyl absorptions consistent with formation of the Ni(CO)$_2$-loaded resin.

IR: NiC—O at 2035, 1984 cm$^{-1}$.

Example 11

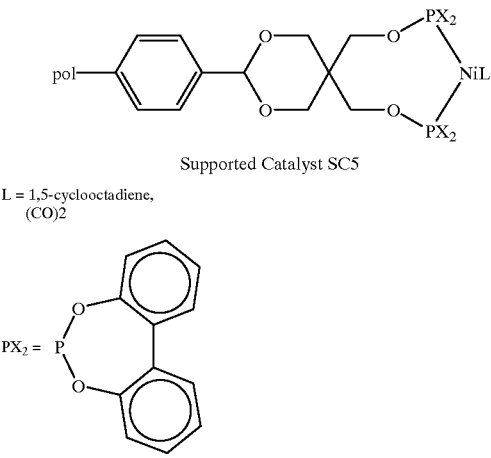

Supported Catalyst SC5

L = 1,5-cyclooctadiene, (CO)2

1.030 g of the supported ligand SL2 was similarly treated with 0.280 g Ni(COD)$_2$ in toluene to yield the Ni(COD)-supported catalyst.

50 mg of the resulting dark brown Ni(COD)-supported catalyst was treated with CO at 1 atm for 2.5 h. After filtration and washing with toluene and pentane the Ni (CO)$_2$-supported resin was dried under vacuum.

IR: 2046, 1987 cm$^{-1}$.

Example 12

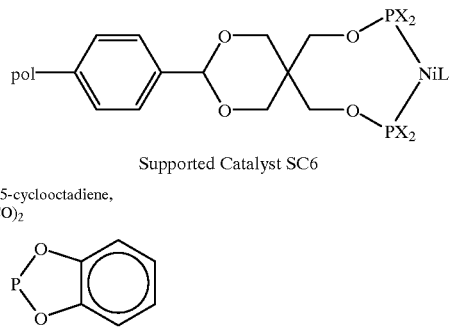

Supported Catalyst SC6

L = 1,5-cyclooctadiene, (CO)$_2$

This catalyst was prepared from supported ligand SL4 and Ni(COD)$_2$ following the procedures described above.

Example 13

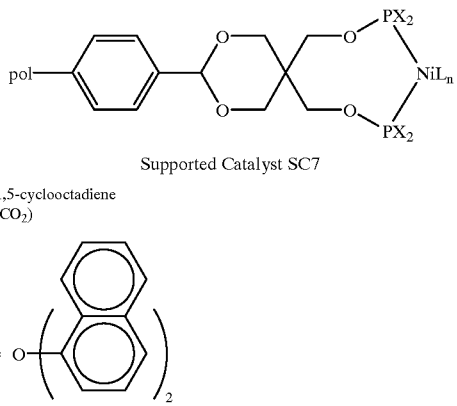

Supported Catalyst SC7

L$_n$ = 1,5-cyclooctadiene (CO$_2$)

Approximately 1.5 g of the bis(phosphite) resin SL5 was suspended in 10 mL of toluene and treated with 0.28 g Ni(COD)$_2$ in a sintered glass filter. The reaction was stirred with a spatula until the resin turned yellow, whereupon the reaction was quickly filtered. The resulting resin was washed with toluene and pentane and dried under vacuum as a yellow solid.

50 mg of the resulting Ni(COD) loaded resin was suspended in 5 mL toluene and treated with 1 atm CO for 20 min. The Ni(CO)$_2$-loaded product was filtered, washed with acetaone and hexane, and then dried under vacuum.

IR (KBr, cm$^{-1}$): 2084 (weak), 2041, 1986.

Example 14

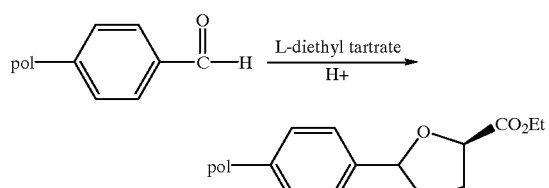

8.0 g of polymer-supported benzaldehyde resin (1% divinylbenzene cross-linked), 3.3 g diethyltartrate, and a few crystals of p-toluenesulfonic acid were combined in 50 mL toluene. The mixture was refluxed for 18 h, with the condensed vapors passing through a bed of molecular sieves before returning to the reaction flask. The resin was collected by filtration, washed with acetone (4×15 mL), CH$_2$Cl$_2$ (4×15 mL), hexane (2×15 mL), and CH$_2$Cl$_2$ before vacuum drying.

IR: —CO$_2$Et at 1730 cm$^{-1}$; complete loss of aldehyde C=O at 1701 cm$^{-1}$.

An identical experiment was conducted using 2% cross-linked resin (86094-57) to give a derivatized resin with an identical infrared spectrum.

Example 15

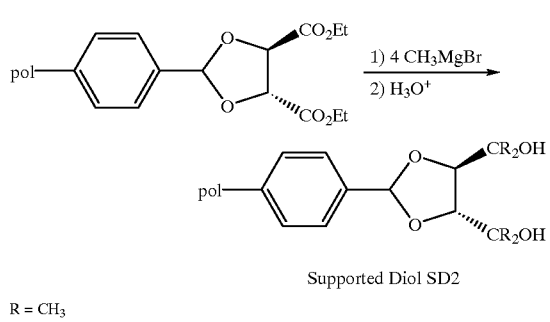

Supported Diol SD2

R = CH$_3$ 7.3 g polymer-supported diester of Example 14 was suspended in 100 mL dry THF and then cooled to 0° C. 11.4 mL of a 3.0 M solution of CH$_3$MgBr in diethyl ether was added dropwise. The mixture was warmed to room temperature and then heated to 60° C. After 3.5 h the mixture was cooled to 0° C. and then quenched with aqueous HCl. The product was collected by filtration, washed with H$_2$O (3×15 mL), acetone (3×15 mL), and diethyl ether (2×15 mL), and finally vacuum dried.

IR: O—H at 3400 cm$^{-1}$; complete loss of the ester band at 1730 cm$^{-1}$.

An identical experiment was conducted using 2% cross-linked resin to give a derivatized resin with an identical infrared spectrum.

Example 16

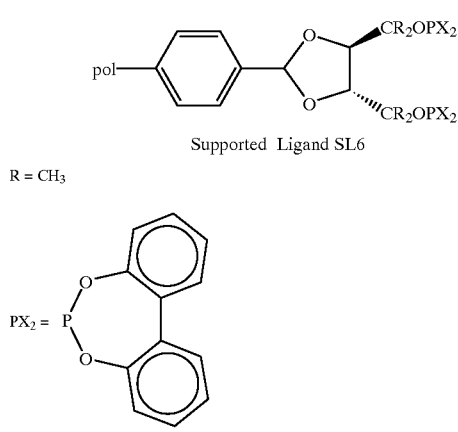

Supported Ligand SL6

R = CH$_3$ 5.374 g of supported diol SD2 was suspended in 50 mL toluene and 15 mL pyridine. 8.04 g 1,1'-biphenyl-2,2'-diylphosphorochloridite (50 wt % soln in toluene) was added dropwise. The mixture was heated overnight at 60° C. The product was filtered, washed with pyridine (2×15 mL), diethyl ether (3×15 mL), and hexane (15 mL) before vacuum drying.

IR: complete loss of O—H at 3400 cm$^{-1}$.
$^{31}$P NMR (CDCl$_3$): 153 ppm.

Example 17

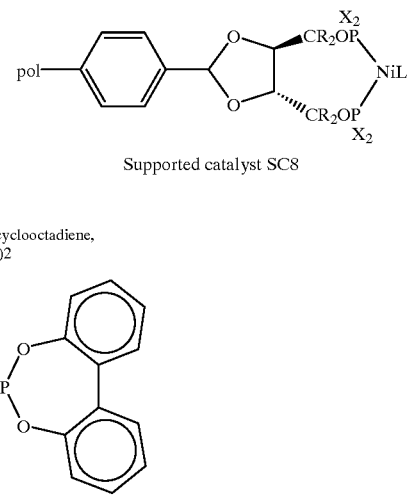

Supported catalyst SC8

R = CH$_3$

L = 1,5-cyclooctadiene, (CO)$_2$ 1.087 g of supported ligand SL6 was suspended in 25 mL toluene and 0.29 g Ni(COD)$_2$ was added. After 3.5 h the product was isolated as a brown solid and washed with toluene (4×10 mL) and pentane (2×10 mL) before vacuum drying.

50 mg of the supported Ni(COD) catalyst was suspended in 10 mL toluene and treated with 1 atm CO for 15 h at room temperature. The resin was then filtered and washed with toluene (3×15 mL) and hexane (2×5 mL). The resulting pale gray solid was then dried under vacuum.

IR (KBr, cm$^{-1}$): 2082 (weak), 2036, 1977.

Example 18

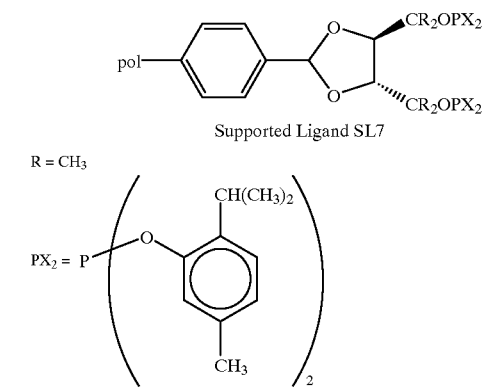

Supported Ligand SL7

R = CH$_3$

Resin-supported diol SD2 (5.0 g) was suspended in a pyridine/toluene (3/1) mixture. 3.82 g bis(2-isopropyl-5-methylphenyl)phosphorochloridite was then added dropwise with stirring at room temperature. After several hours the resin was filtered and washed with pyridine (4×25 mL), diethyl ether (2×25 mL), and pentane (2×25 mL) before vacuum drying.

IR: complete loss of O—H band.

Example 19

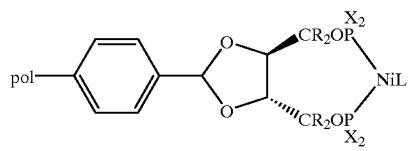

Supported Catalyst SC9

R = CH₃
L = 1,5-cyclooctadiene, (CO)₂

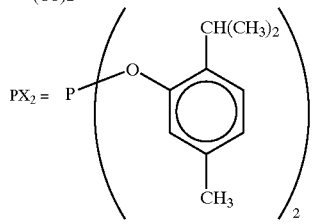

Resin-supported ligand SL7 (1.235 g) was suspended in 15 mL toluene and 0.279 g Ni(COD)₂ was added. The mixture was stirred for 2 h at room temperature and then filtered. The dark solid was washed with toluene and pentane, and then vacuum dried.

50 mg of the resulting Ni(COD)-loaded catalyst was placed in 10 mL toluene and treated with 1 atm CO at room temperature for 3 days. The product was washed with hexane (4×10 mL) and dried under vacuum.

IR: NiC—O at 2032 and 1977 cm⁻¹.

Example 20

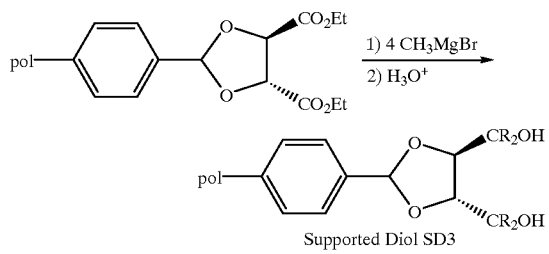

Supported Diol SD3

R = Ph

The resin-supported diester of Example 14 (10.98 g) was suspended in 50 mL THF at 0° C. 18.4 mL of PhMgBr (3.0 M solution in diethyl ether) was then added, with stirring. When the addition was complete the suspension was gradually warmed to 60° C. and maintained at this temperature for 15 h. After cooling to 0° C. the reaction was quenched with dilute aqueous HCl and the product collected by filtration. After washing with H₂O (5×25 mL), acetone (5×25 mL), and hexane (3×25 mL), it was vacuum dried.

IR: O—H at 3400 cm⁻¹; complete loss of ester C=O at 1730 cm⁻¹.

Example 21

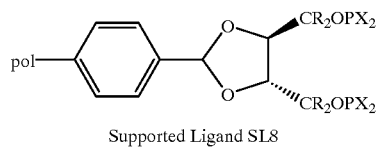

Supported Ligand SL8

R = Ph
PX₂ = PPh₂

Resin-supported diol SD3 (2.344 g) was suspended in 20 mL of pyridine/toluene (1/1). 1.12 g PPh₂Cl was added dropwise; heat evolution was noted. After stirring for 3 days at room temperature the reaction was heated to 80° C. overnight. The product was collected by filtration, washed with pyridine (3×15 mL), and pentane (3×15 mL) and then dried under vacuum.

IR: loss of O—H band.

Example 22

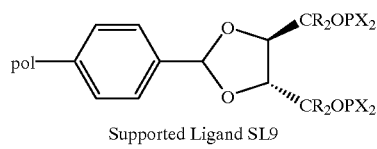

Supported Ligand SL9

R = Ph

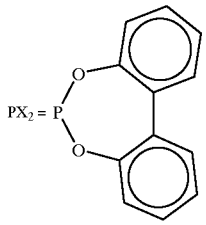

This material was prepared and isolated in a similar fashion using 2.257 g of supported diol SD3 and 2.44 g 1,1'-biphenyl-2,2'-diylphosphorochloridite (50 wt % solution in toluene).

IR: loss of O—H band.

Example 23

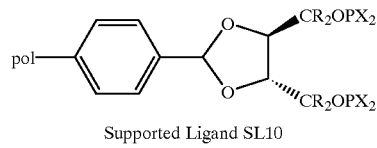

Supported Ligand SL10

R = Ph

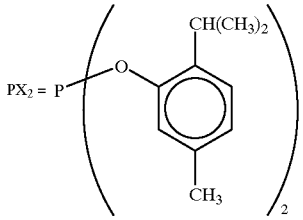

This material was prepared and isolated in a similar fashion using 2.250 g of supported diol SD3 and 1.769 g bis(2-isopropyl-5-methylphenyl)phosphorochloridite (as a toluene solution).

IR: loss of O—H band.

Example 24

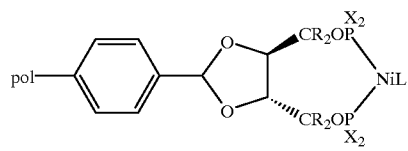

Supported catalyst SC10

R = Ph
L = 1,5-cyclooctadiene, (CO)2
$PX_2$ = $PPh_2$

Resin-supported ligand SL8 (1.90 g) was suspended in 20 mL toluene. 0.445 g of Ni(COD)$_2$ was added. After 3 h the catalyst, a nearly black solid due to some precipitated Ni metal, was isolated by filtration and washed thoroughly with toluene, pentane, and then vacuum dried.

A small amount of the resulting catalyst was suspended in toluene and treated with CO (1 atm) at room temperature for 3 h. The dark brown resin was isolated by filtration, washed with hexane and dried under vacuum.

IR: 2067, 1996 cm$^{-1}$.

Example 25

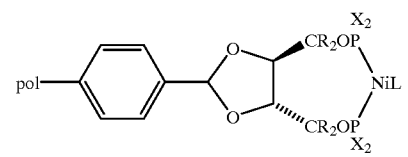

Supported Catalyst SC11

L = 1,5-cyclooctadiene, (CO)2
R = Ph

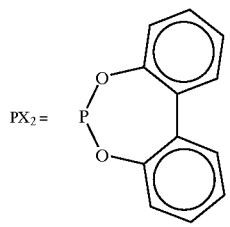

In a similar fashion, resin supported catalyst SC11 was prepared from 1.50 g of supported ligand SL9 and 0.340 g Ni(COD)$_2$ to yield a light brown solid.

A portion of this material was similarly treated with CO in toluene to give a beige solid.

IR: 2083; 2042; 2006; 1987 cm$^{-1}$.

Example 26

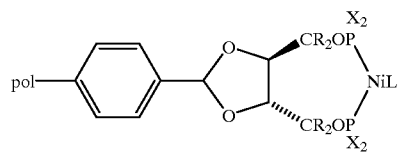

Supported Catalyst SC12

L = 1,5-cyclooctadiene, (CO)2
R = Ph

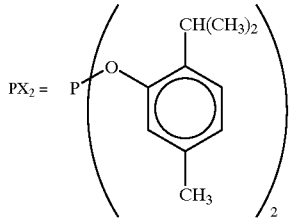

Similarly, resin-supported ligand SL10 (1.60 g) was treated with 0.32 g Ni(COD)$_2$ in 20 mL toluene. Work-up provided the Ni(COD) catalyst as a brown solid.

A small amount of this material was treated with CO in toluene per the above procedure.

IR: 2080; 2035; 2010; 1980 cm$^{-1}$.

Example 27

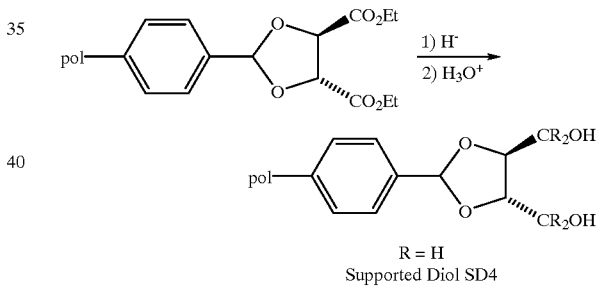

R = H
Supported Diol SD4

6.66 g of the resin-supported diester of Example 14 in 60 mL of THF was treated with 34.3 mL of a 1.0 M solution of LiBHEt$_3$ in THF. After 5 h at room temperature the reaction was quenched (95% ethanol or isopropanol) and the resulting resin isolated by filtration. The resin was dried under vacuum after washing with water, alcohol, and then diethyl ether.

IR: formation of O—H at 3400 cm$^{-1}$; complete loss of ester C=O band at 1730 cm$^{-1}$.

Example 28

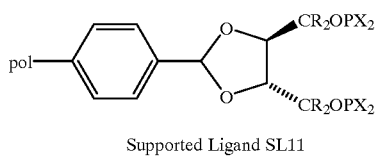

Supported Ligand SL11

-continued

R = H

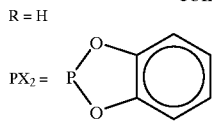

1.54 g of resin-supported diol SD4 was suspended in 10 mL toluene and 0.788 g of 1,2-phenylene phosphorchloridite was added, followed by 1 mL pyridine. The suspension was stirred at room temperature for 3 days and 1 day at 40° C. The product was isolated by filtration, washed with three portions of pyridine, then with pentane, and dried under vacuum.

The corresponding Ni(COD)-loaded catalyst SC13 was prepared in the usual manner from supported ligand SL11 and characterized as the supported dicarbonyl derivative. IR (KBr, cm$^{-1}$): 2091 (weak), 2055, 2006.

THF was added dropwise. The suspension was warmed to room temperature and stirred for 1.5 h. The reaction was quenched by the addition of isopropanol. The resin was isolated by filtration, washed with isopropanol and hexane, and dried under vacuum. The resin was then suspended in 20 mL EtOH and treated with aqueous NaOH (0.6 g in 5 mL water) and 15 mL 30% $H_2O_2$. After stirring overnight at room temperature the resin was filtered and washed with ethanol/aqueous HCl, ethanol, acetone, ether, and hexane, and then vacuum dried.

IR: O—H at 3400 cm$^{-1}$; complete loss of C=O at 1701 cm$^{-1}$.

Example 30

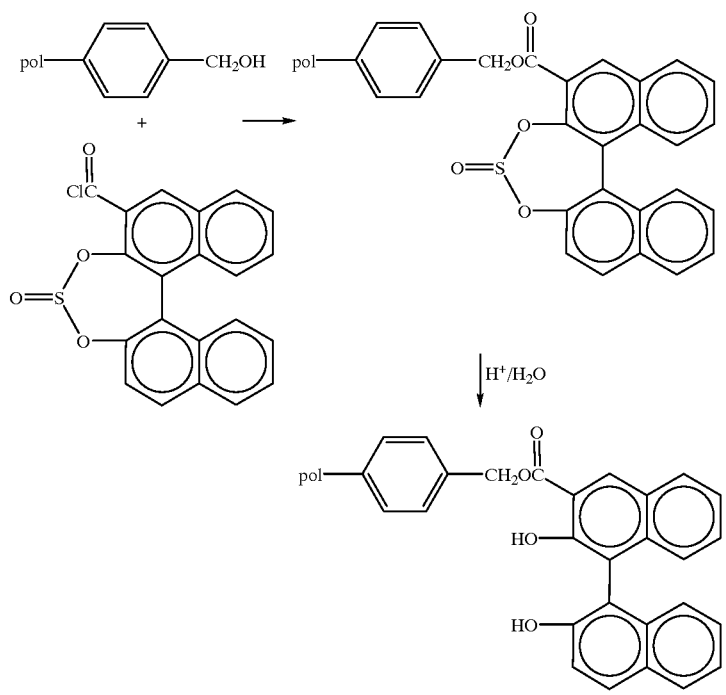

Supported Diol SD5

Example 29

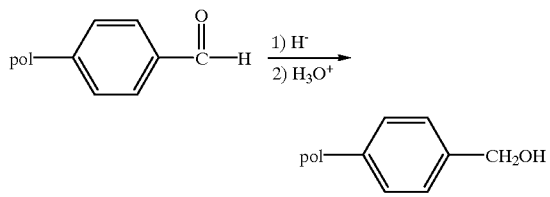

This supported benzyl alcohol can be purchased commercially from Novabiochem Corp., LaJolla, Calif. or prepared by the following method. 10.33 g of polymer-supported benzaldehyde resin was suspended in 100 mL THF and cooled to 0° C. 15.4 mL of a 1.0 M solution of LiBHEt$_3$ in 0.525 g of the / resin-supported benzyl alcohol (2% divinylbenzene cross-linking) was suspended in 15 mL THF and then treated with 0.236 g of the sulfoxyl-protected binaphthol acid chloride shown. The sulfoxyl-protected binaphthol acid chloride was prepared by oxidative coupling of 2-naphthol with 2-hydroxy-3-naphthoic acid followed by treatment with thionyl chloride. These transformations are well known to those skilled in the art. The mixture was stirred for 1 day at room temperature and then one day at 45° C. The reaction was quenched with $H_2O$/methanol, filtered, and the resin washed with toluene, acetone, methanol, water, acetone, and hexane before vacuum drying.

IR: O—H at 3430 cm$^{-1}$, ester C=O at 1729 cm$^{-1}$.

Example 31

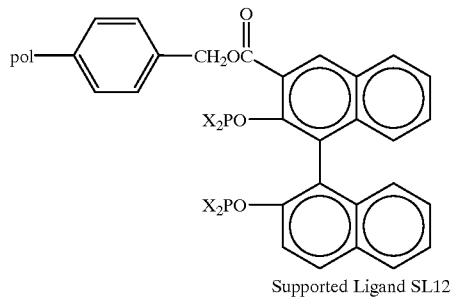

Supported Ligand SL12

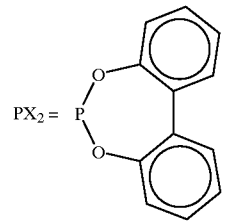

The resin-supported diol SD5 (1.80 g) was suspended in 15 mL of THF along with 1 mL of pyridine and 2.70 g of 1,1'-biphenyl-2,2'-diylphosphorochloridite (50 wt % solution in toluene). The mixture was stirred overnight at 50° C. before filtration. The product was washed with $CH_2Cl_2$ (3×5 mL), THF (3×5 mL), toluene (3×5 mL), and pentane (2×5 mL), before vacuum drying.

IR showed nearly complete loss of O—H at ca. 3400 $cm^{-1}$. $^{31}P\{^1H\}$ MAS NMR ($CDCl_3$): broad resonances at $\delta 144.2$ and $137.8$, in addition to an unidentified component at $\delta 12.8$.

Example 32

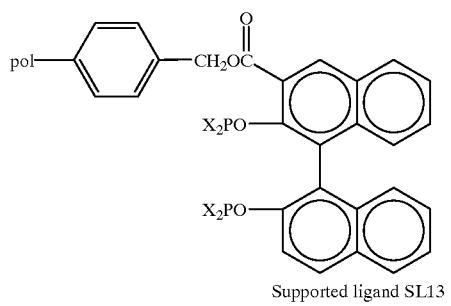

Supported ligand SL13

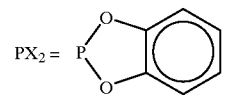

Resin SD5 (1.74 g) was suspended in 15 mL of THF. To this was added 0.91 g of 1,2-phenylenephosphorochloridite and 1 mL of pyridine, and the mixture was stirred overnight at 50° C. The resin was collected by filtration and washed with successive portions of $CH_2Cl_2$, THF, toluene, and pentane before vacuum drying.

$^{31}P\{^1H\}$ MAS NMR ($CDCl_3$): $\delta 130.6$ (major), 127.0 (minor), in addition to several unidentified resonances at $\delta 74, 45$, and 22 to −20.

Example 33

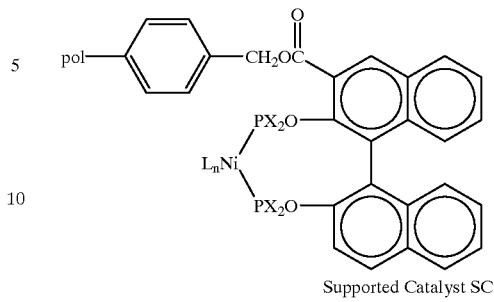

Supported Catalyst SC14

$L_n$ = 1,5-cyclooctadiene ($CO_2$)

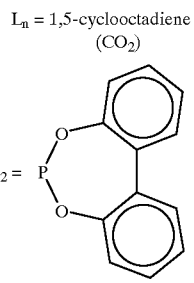

The resin-supported ligand SL12 (1.105 g) was suspended in 8 mL of toluene and then treated with 0.19 g $Ni(COD)_2$. The black Ni(COD)-loaded catalyst was isolated by filtration, washed with toluene and pentante, and then vacuum dried.

0.1 g of the Ni(COD)-loaded catalyst SC14 was treated with 1 atm CO in 5 mL of toluene for 30 min. The black solid was isolated by filtration and washed with acetone and hexane before vacuum drying.

IR (KBr, $cm^{-1}$): 2083 (weak), 2047, 1998.

Example 34

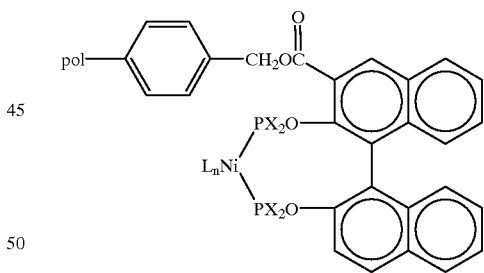

Supported Catalyst SC15

$L_n$ = 1,5-cyclooctadiene ($CO_2$)

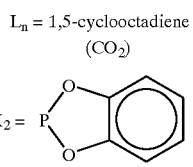

The resin-supported ligand SL13 (1.02 g) was suspended in 8 mL of toluene and then treated with 0.19 g $Ni(COD)_2$ for 40 min at room temperature. The Ni(COD)-loaded catalyst was filtered and washed with toluene and pentane, then vacuum dried, to give a black solid.

0.1 g of the resulting catalyst SC15 was suspended in 5 mL toluene and treated with 1 atm CO and stirring for 30 min. The resulting dark brown Ni(CO)$_2$-loaded resin was filtered and then washed with acetone and hexane before vacuum drying.

IR (KBr, cm$^{-1}$): 2090 (weak), 2060, 2012.

Example 35

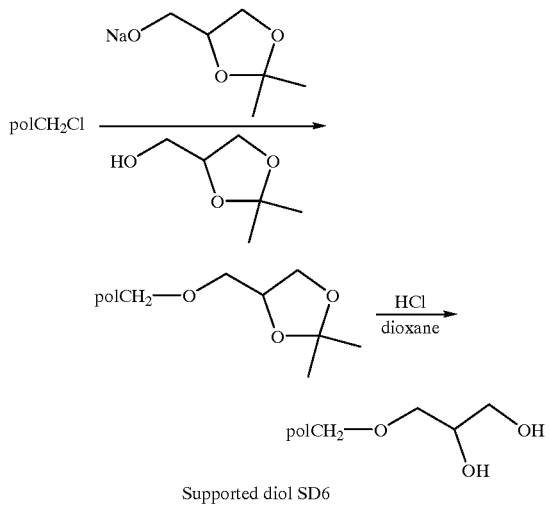

Supported diol SD6

This supported diol was prepared by the literature procedure in Can. J. Chem., 1973, 51, 3756. 18.8 g of Merrifield resin was suspended in 50 mL of solketal containing 4.70 g of the sodium salt of solketal. The mixture was stirred overnight at 80° C. The intermediate ketal was collected by filtration, and then washed with water (3×20 mL), acetone (3×20 mL), and hexane (3×20 mL).

IR(KBr): C—O—C at 1151, 1211, 1249 cm$^{-1}$. $^{13}$C{$^1$H} MAS NMR (CDCl$_3$): δ110.1, 75.5, 74.6, 71.6, 67.7.

The supported ketal was deprotected by suspension in 200 mL of dioxane containing a small amount of 10% aq HCl. The mixture was stirred overnight at room temperature. Workup was accomplished by filtration and then washing with water, acetone, and THF before vacuum drying.

IR: (KBr): Loss of): C—O—C at 1156–1249 cm$^{-1}$; formation of O—H at 3430 cm$^{-1}$. $^{13}$C{$^1$H} MAS NMR (CDCl$_3$): δ74.2, 72.2, 71.6, 64.8, in addition to polymer resonances.

Example 36

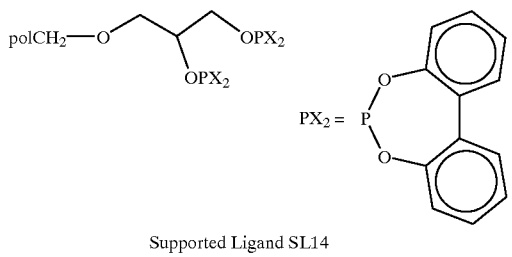

Supported Ligand SL14

1.185 g of the supported diol resin SD6 was suspended in 15 mL of THF. 1.8 g of 1,1'-biphenyl-2,2'-diylphosphorochloridite (50 wt % solution in toluene) was added dropwise, followed by 1.0 mL of pyridine. The resulting mixture was stirred at room temperature for 3 days. The product was isolated by filtration and then washed with successive portions of CH$_3$CN, CH$_2$Cl$_2$, and pentane. The product was then vacuum dried.

IR (KBr): disappearance of O—H at 3430 cm$^{-1}$. $^{31}$P{$^1$H} MAS NMR (CDCl$_3$): δ144.4, 138.3, in addition to minor components between δ25–7.

Example 37

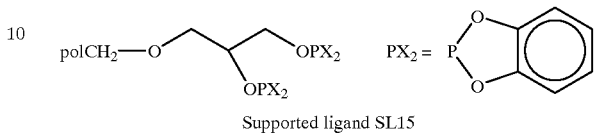

Supported ligand SL15

1.40 g of the resin-supported diol SD 6 was suspended in 15 mL of THF and then treated with 0.75 g 1,2-phenylenephosphorochloridite and 1 mL of pyridine. The resulting mixture was stirred for three days at room temperature. The product was filtered, washed with CH$_2$Cl$_2$, toluene, and pentane, and then dried under vacuum.

IR (KBr): disappearance of O—H at 3430 cm$^{-1}$. $^{31}$P{$^1$H} MAS NMR (CDCl$_3$): δ144.2, 138.2.

Example 38

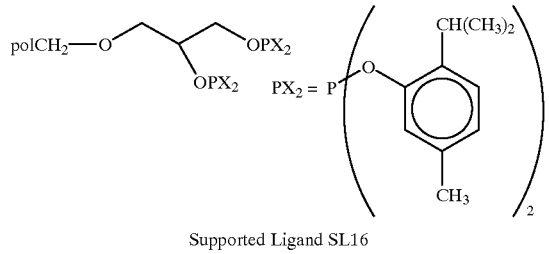

Supported Ligand SL16

1.40 g of supported diol resin SD6 was suspended in 15 mL of THF and then treated with 1.53 g of bis(2-isopropyl-5-methylphenyl)phosphorochloridite (as a toluene solution) and 1 mL of pyridine. The mixture was stirred for 3 days at room temperature. The product was filtered, washed with CH$_2$Cl$_2$, CH$_3$CN, and pentane before vacuum drying.

IR (KBr): disappearance of O—H at 3430 cm$^{-1}$. $^{31}$P{$^1$H} MAS NMR (CDCl$_3$): δ131.0, 128.6, in addition to several minor components in the ranges δ134–127 and δ25–0. Elemental analysis: 81.44% C, 7.83% H, 3.09% P.

Example 39

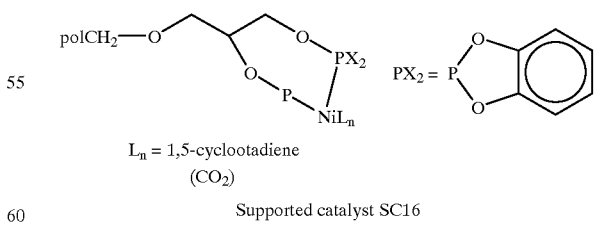

L$_n$ = 1,5-cyclootadiene
(CO$_2$)

Supported catalyst SC16

Method 1. 0.55 g of the bis(phosphite)-supported resin SL15 was suspended in 15 mL of toluene in a sintered glass suction filter. A toluene solution of 0.19 g Ni(COD)$_2$ (1.5 equiv) was added and the mixture was stirred with a spatula. After approximately 1 minute the resin began to turn brown.

The solvent was filtered away and the resin was washed with toluene and pentane before vacuum drying to yield the catalyst as a brown solid.

A small amount of the resulting Ni(COD)-loaded catalyst was suspended in 5 mL of toluene and then treated with 1 atm of CO. After 20 min the resin turned beige. The resin was collected by filtration, washed with acetone and then hexane before vacuum drying.

IR (KBr, cm$^{-1}$): 2089 (very weak), 2056, 2004.

Method 2. In a small vial, 0.50 g of the bis(phosphte)-supported resin SL15 was suspended in 5 mL toluene containing 0.18 g Ni(COD)$_2$. The mixture was stirred for 20 min, during which time the resin turned black. The catalyst resin was filtered and then washed with toluene and pentane before vacuum drying.

A small amount of the resulting Ni(COD)-loaded catalyst was then treated with CO in the same manner described above to give the Ni(CO)$_2$-loaded resin as a black material.

IR (KBr, cm$^{-1}$): identical to that derived in Method 1.

Example 40

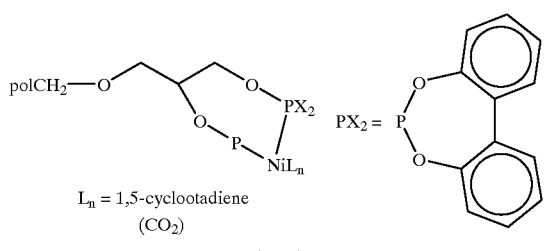

Supported catalyst SC17

Method 1. The same procedure described in Example 39 Method 1 was followed using 0.46 g of resin SL14 and 0.144 g Ni(COD)$_2$ to give the Ni(COD)-loaded catalyst resin as a light purple solid.

Treatment with CO by the method described yielded the Ni(CO)$_2$-loaded resin as a colorless solid.

IR (KBr, cm$^{-1}$): 2083 (very weak), 2042, 2015 (shoulder), 1988.

Method 2. The same procedure described for Example 39 Method 2 was followed using 0.45 g of resin SL14 and 0.144 g Ni(COD)$_2$ to give the Ni(COD)-loaded catalyst resin as a dark brown solid.

Treatment with CO by the method described yielded the Ni(CO)$_2$-loaded resin as a dark brown solid.

IR (KBr, cm$^{-1}$): identical to that obtained by Method 1.

Example 41

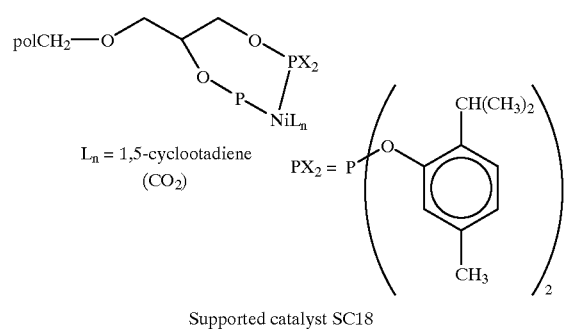

Supported catalyst SC18

Method 1. The same procedure described for Example 39 Method 1 was followed using 0.497 g of resin SL16 and 0.14 g Ni(COD)$_2$ to give the Ni(COD)-loaded catalyst resin as a brown solid.

Treatment with CO by the method described yielded the Ni(CO)$_2$-loaded resin as a beige solid.

IR (KBr, cm$^{-1}$): 2080 (very weak), 2040, 1988.

Method 2. The same procedure described for Example 39 Method 2 was followed using 0.514 g of resin SL16 and 0.14 g Ni(COD)$_2$ to give the Ni(COD)-loaded resin as a black solid.

Treatment with CO by the method described yielded the Ni(CO)$_2$-loaded resin as a black solid.

IR (KBr, cm$^{-1}$): identical to that obtained by Method 1.

Example 42

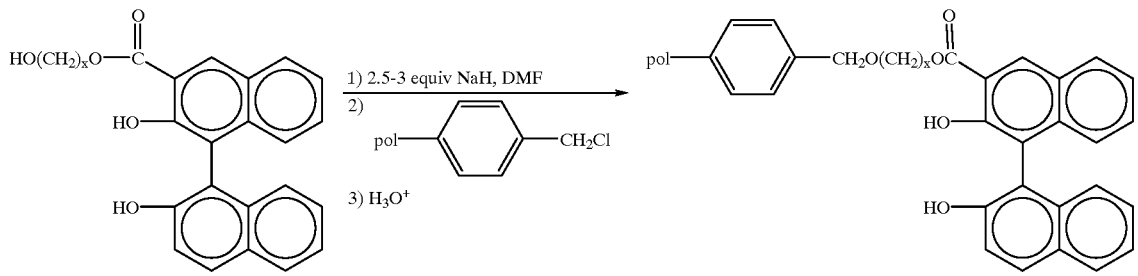

Example 42-1, x = 3, Supported diol SD7

2.33 g of the binaphthol ester shown (x=3) was dissolved in DMF. 0.39 g (2.7 equiv) of NaH was added to give gas evolution and an orange solution. After 20 min at room temperature the solution was treated with 4.0 g of Merrifield's resin (4.8 mmol $CH_2Cl$). The mixture was stirred overnight at 98° C. The resulting resin was isolated by filtration and then washed with 95% EtOH, acetone, THF, toluene, and hexane before drying under vacuum.

IR (KBr, $cm^{-1}$): 3441 and 3223 (O—H), 1685 (C=O).

Example 42-2 x=4, Supported Diol SD8

In a similar manner, 5.83 g of the binaphthol monoester (x=4), 0.94 g NaH, and 9.6 g of Merrifield's resin were reacted in 30 mL of DMF. After heating at 80° C. overnight the resin was isolated and rinsed by the method described above.

IR (KBr, $cm^{-1}$): 3583, 3419 and 3223 (O—H), 1674 (C=O).

Example 42-3 x=2, Supported Diol SD9

This resin was prepared and isolated similarly from 1.20 g of the binaphthol monoester (x=2), 0.22 g of NaH, and 2.4 g of Merrifield's resin.

IR (KBr, $cm^{-1}$): 3451, 1690 (C=O).

Example 43

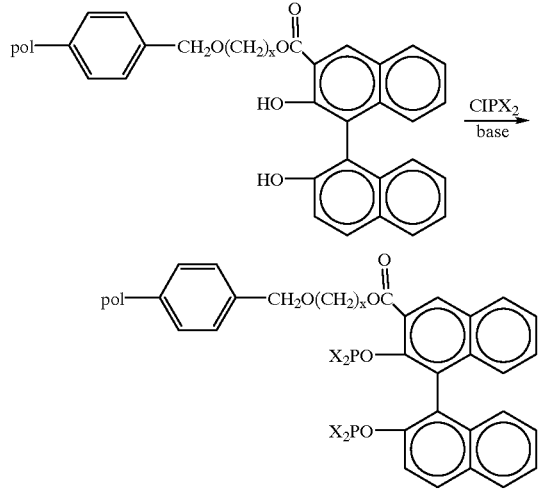

SL 17-22

The following is a general example for the synthesis of this class of supported bis(phosphite) ligands and catalysts. Examples of supported ligands and catalysts prepared by this generic route are provided in Table 1.

Example 43-1 x=4, $X_2$=1,1'-biphenoxy.

The binaphthol-supported resin SD8 from Example 42-2 (2.0 g) was suspended in 10 mL of THF; 3 mL of pyridine and 2.5 g of a 50 wt % solution of 1,1'-biphenyl-2,2'-diylphosphorochloridite in toluene were then added. The yellow resin decolorized immediately. The mixture was stirred overnight at room temperature and then worked up by filtration and washing the resin with pyridine, THF, and pentane. The light yellow supported ligand SL17 was dried under vacuum.

The Ni(COD)-loaded catalysts were prepared and analyzed as the $Ni(CO)_2$ derivatives by the methods described in previous examples.

TABLE 1

| Example | x | X2 | Supported ligand code |
|---------|---|----|-----------------------|
| 43-2 | x = 3 | 1,1'-biphenoxy | SL18 |
| 43-3 | x = 3 | 1,2-phenylenedioxy | SL19 |
| 43-4 | x = 4 | 1,2-phenylenedioxy | SL20 |
| 43-5 | x = 2 | 1,1'-biphenoxy | SL21 |
| 43-6 | x = 2 | 1,2-phenylenedioxy | SL22 |
| 43-7 | x = 3 | SL18 + $Ni(COD)_2$ | SC19 |
| 43-8 | x = 4 | SL17 + $Ni(COD)_2$ | SC20 |
| 43-9 | x = 3 | SL19 + $Ni(COD)_2$ | SC21 |
| 43-10 | x = 4 | SL20 + $Ni(COD)_2$ | SC22 |
| 43-11 | x = 2 | SL21 + $Ni(COD)_2$ | SC23 |
| 43-12 | x = 2 | SL22 + $Ni(COD)_2$ | SC24 |

Example 44

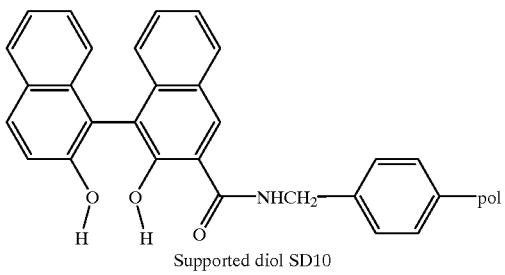

Supported diol SD10

The sulfoxyl-protected binaphthol acid chloride shown in Example 30 (5.9 g, 15 mmol) was dissolved in 150 mL of dry DMF. The commercially available benzyl amine resin (6.1 g, 6 mmol) from Novabiochem. Corp. and then diisopropyl ethyl amine (DIEA) (26 mL, 150 mmol) were added. The mixture was agitated on a Rotovap over night with exclusion of air. Water (4 mL, 220 mmol) was added to the reaction mixture and the suspension was rotated for another 3 h. The resin was filtered, washed with DMF thoroughly, then with $CH_2Cl_2$ and hexanes before vacuum drying.

IR(KBr): OH and NH at 3422 $cm^{-1}$ (br) and 3535 $cm^{-1}$ (shoulder), amide at 1652 $cm^{-1}$.

Example 45

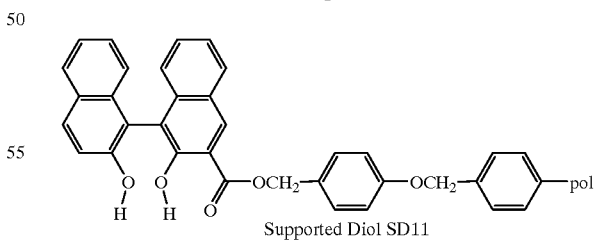

Supported Diol SD11

The same procedure described in Example 44 was employed with 10 g (6.9 mmol) of commercially available Wang resin (from Advanced Chemtech, Louisville, Ky.), 8.2 g (20.7 mmol) of the sulfoxyl-protected binaphthol acid chloride shown in Example 30, and 36 ml of DIEA.

IR (KBr): OH at 3443 $cm^{-1}$ (br) ester at 1678 $cm^{-1}$ (s)

Example 46

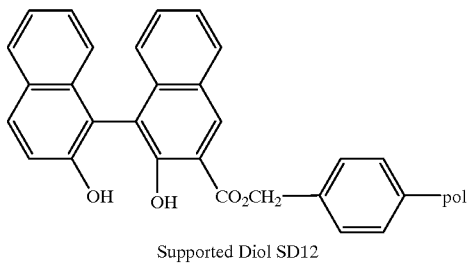

Supported Diol SD12

The same procedure described in Example 44 was used using 6 g (7 mmol) of / (21 mmol) of sulfoxyl-protected binaphthol acid chloride, and 6.1 ml of DIEA.

IR (KBr): OH at 3448 cm$^{-1}$ (br) and 3247 cm$^{-1}$ (br), ester at 1740 cm$^{-1}$ (m).

Example 47

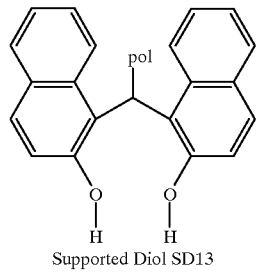

Supported Diol SD13

The resin-supported benzaldehyde described in Example 1 (407 mg, 0.5 mmol), 2-naphthol (576-mg, 2 mmol), glacial acetic acid (5 ml), CHCL$_3$ (1 ml) and hydrochloric acid (0.5 ml) were mixed with a vortexer for 5 days. The product was filtered, washed with aqueous THF, and then THF thoroughly before vacuum drying.

Example 48

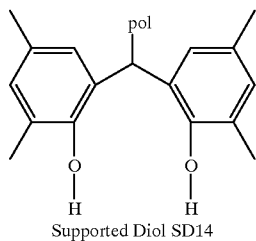

Supported Diol SD14

2,4-Dimethylphenol (6.95 ml, 57.6 mmol) and resin-supported benzaldehyde (5.85 g, 7.2 mmol) were added to an ice cold aqueous sulfuric acid solution (H$_2$SO$_4$: 15 ml; H$_2$O 12 ml). The reaction mixture was shaken until no starting material was observed in the IR spectrum. The resin was collected by filtration, washed with aqueous acetone, aqueous THF, and thoroughly with THF before vacuum drying.

IR (KBr): OH at 3444 cm$^{-1}$ (br, s).

Example 49

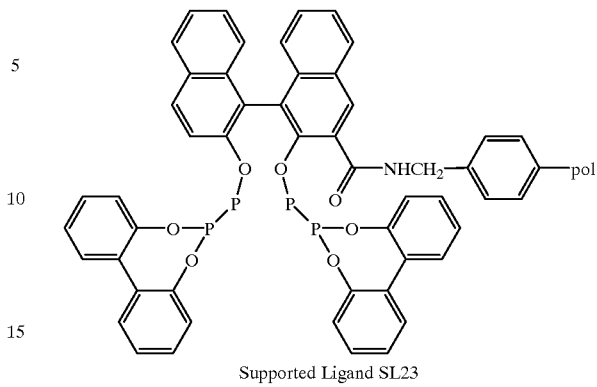

Supported Ligand SL23

DIEA (1.7 ml, 10 mmol) was added to the suspension containing the resin-supported diol SD10 (1.33 g, 1.0 mmol), 2.0 g (4.0 mmol) of 1,1'-biphenyl-2,2'-diylphosphorochloridite (50% weight in toluene) and 10 ml of dry toluene. The resulting mixture was vortexed at room temperature overnight. The brown product was filtered, washed with toluene, DMF, CH$_2$Cl$_2$, hexanes and vacuum dried to lead to a fluffy solid.

IR(KBr): NH at 3433 cm$^{-1}$ (m), amide at 1659 cm$^{-1}$(s)
Elemental Analysis: C% 83.27, H% 6.61, N% 1.06, P% 2.12

Example 50

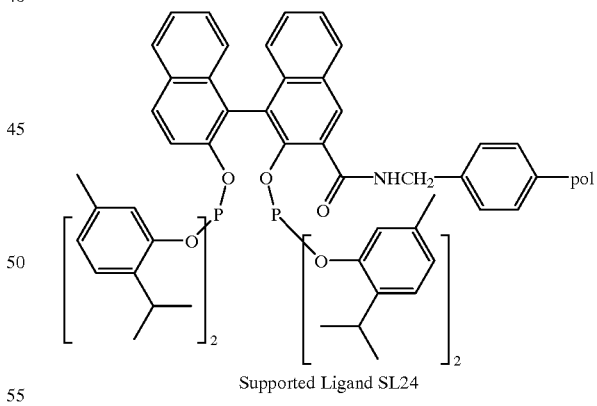

Supported Ligand SL24

This ligand was prepared according to the same procedure as that of Example 49 using 1.46 g (4.0 mmol) of bis(2-isopropyl-5-methylphenyl)phosphorochloridite.

IR (KBr): NH at 3431 cm$^{-1}$ (m), amide at 1666 cm$^{-1}$ (s).
Elemental Analysis: C% 84.01, H% 7.07, N% 1.25, P% 1.53

Example 51

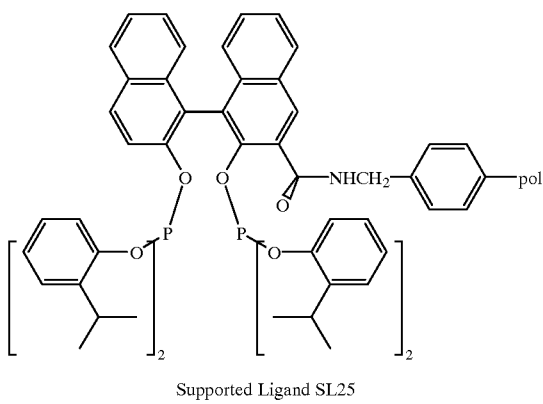

Supported Ligand SL25

This product was synthesized following the procedure described for Example 49 using 1.34 g of bis(2-isopropylphenyl)phosphorochloridite and the same amounts of the resin, DIEA and toluene.

IR (KBr): NH at 3432 cm$^{-1}$ (s), amide at 1656 cm$^{-1}$ (s) Elemental Analysis: C% 83.25, H% 6.97, N% 1.30, P% 1.56

Example 52

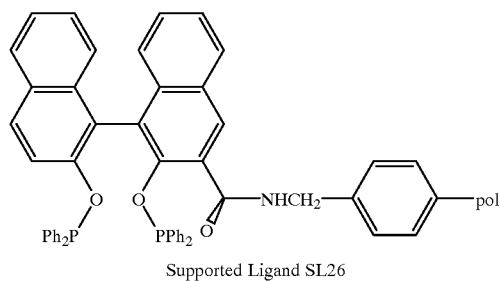

Supported Ligand SL26

The same procedure described for Example 49 was followed using 0.718 ml (4 mmol) of chlorodiphenylphosphine.

IR (KBr): NH at 3422 cm$^{-1}$ (s), amide at 1656 cm$^{-1}$ (s) Elemental Analysis: C% 85.94, H% 6.57, N% 1.28, P% 2.01

Example 53

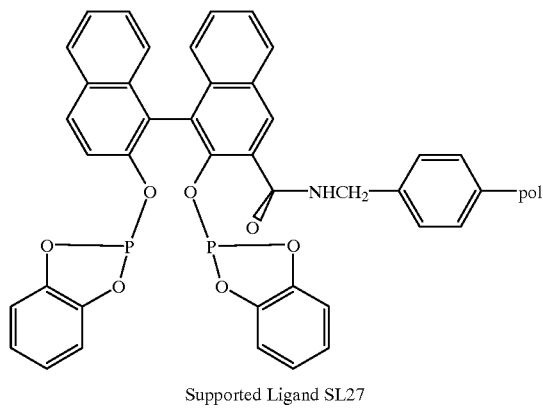

Supported Ligand SL27

This ligand was synthesized according to the same procedure as that for Example 49 using 698 mg (4.0 mmol) of 1,2-phenylenephosphorochloridite.

IR (KBr): NH at 3437 cm$^{-1}$ (m), amide at 1667 cm$^{-1}$ (s) Elemental Analysis: C% 82.24, H% 6.26, N% 1.19, P% 2.54

Example 54

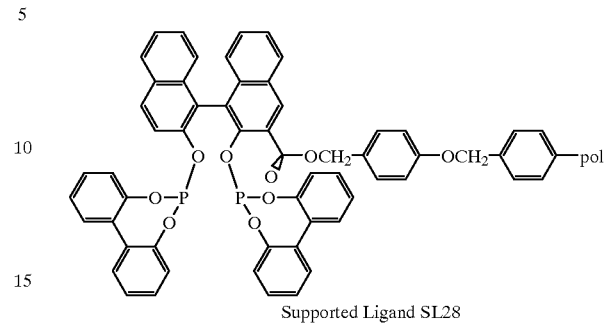

Supported Ligand SL28

This product was obtained following the same procedure described for Example 49 using 2.17 g (1.0 mmol) of resin-supported diol SD11, 2 g of 1,1'-biphenyl-2,2'-diylphosphorochloridite (50% weight in toluene, 4.0 mmol), 1.7 ml (10 mmol) of DIEA and 15 ml of anhydrous toluene.

IR (KBr): 1743 cm$^{-1}$ (vs), 1680 cm$^{-1}$ (m). Elemental Analysis: C% 86.34, H% 7.00, P% 0.77

Example 55

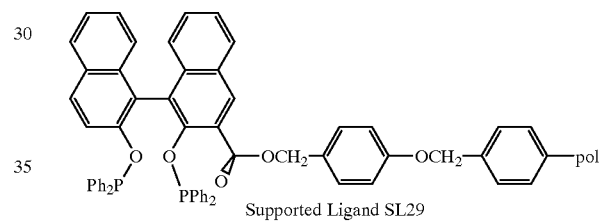

Supported Ligand SL29

This compound was made according to the procedure described for Example 49 using 2.17 g (1.0 mmol) of supported diol SD11, 884 mg (4.0 mmol) of the chlorodiphenylphosphine, 1.7 ml (10 mmol) and 15 ml of toluene.

IR (KBr): 1744 cm$^{-1}$ (m), 1680 cm$^{-1}$ (s) Elemental Analysis: C% 86.55, H% 6.85, P% 0.59

Example 56

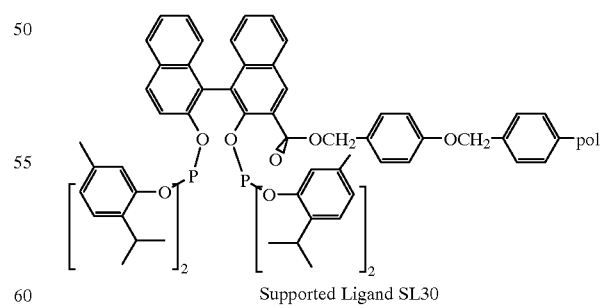

Supported Ligand SL30

The same procedure described for Example 49 was followed using 2.17 g (1.0 mmol) of the resin SD11, 1.46 g (4.0 mmol) of bis(2-isopropyl-5-methylphenyl) phosphorochloridite, 1.7 ml (10 mmol) of DIEA and 15 ml of toluene.

IR (KBr): 1744 cm$^{-1}$ (vs), 1680 cm$^{-1}$ (m) Elemental Analysis: C% 85.49, H% 7.04, P% 0.64

Example 57

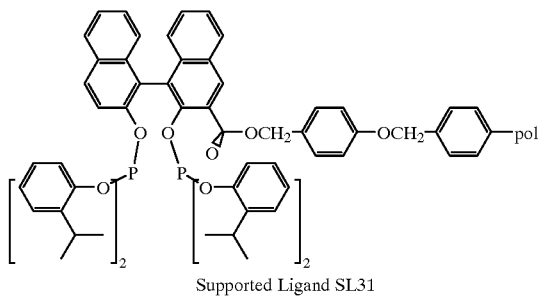

Supported Ligand SL31

The same procedure described for Example 49 was followed using 2.17 g (1.0 mmol) of supported diol SD11, 1.34 g (4.0 mmol) of bis(2-isopropylphenyl)phosphorochloridite, 1.7 ml (10 mmol) Of DIEA and 15 ml of toluene.

IR (KBr): 1722 cm$^{-1}$ (w), 1678 cm$^{-1}$ (m) Elemental Analysis: C% 86.51, H% 7.12, P% 0.42

Example 58

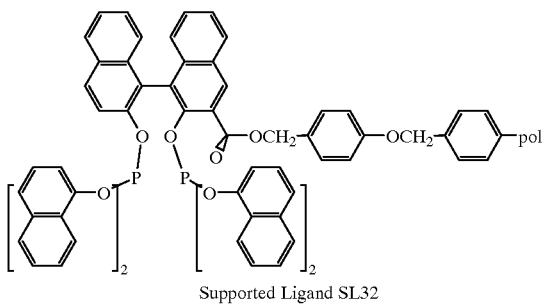

Supported Ligand SL32

This ligand was made following same procedure described for Example 49 from 2.17 g (1.0 mmol) of the supported diol SD11, 1.41 g (4.0 mmol) of bis(1-naphthyl)phosphorochloridite, 1.7 ml (10 mmol) of DIEA and 14 ml of toluene.

IR (KBr): 1726 cm$^{-1}$ (m), 1674 cm$^{-1}$ (w) Elemental Analysis: C% 84.97, H% 8.23, P% 0.55

Example 59

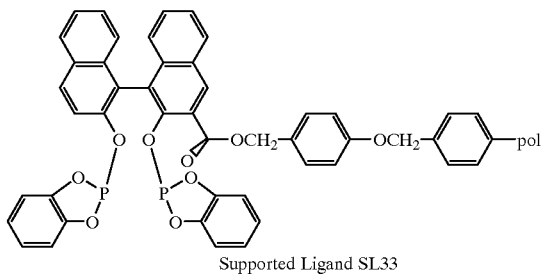

Supported Ligand SL33

The same procedure described for Example 49 was followed using 2.17 g (1.0 mmol) of the resin-supported diol SD11, 884 mg (4.0 mmol) of 1,2-phenylenephosphorochloridite, 1.7 ml (10 mmol) of DIEA and 14 ml of toluene.

IR (KBr): 1726 cm$^{-1}$ (m), 1674 cm$^{-1}$ (w) Elemental Analysis: C% 85.35, H% 6.57, P% 0.51

Example 60

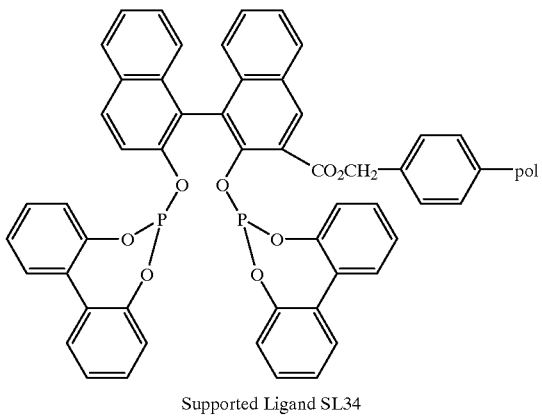

Supported Ligand SL34

The ligand was prepared following the same procedure described for Example 49 using 1.17 g (1.0 mmol) of supported diol SD12, 2 g (50% weight in toluene) (4.0 mmol) of 1,1'-biphenyl-2,2'-diylphosphorochloridite, 1.7 ml (10 mmol) of DIEA and 10 ml of toluene.

IR (KBr): 1742 cm$^{-1}$ (vs), 1680 cm$^{-1}$ (m) Elemental Analysis: C% 84.69, H% 6.51, P% 1.03

Example 61

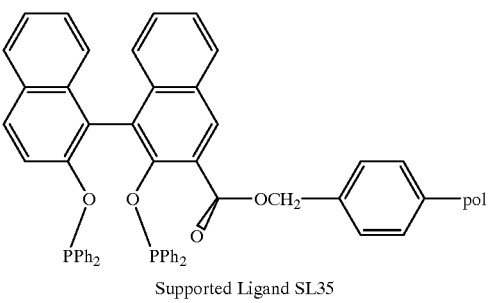

Supported Ligand SL35

The same procedure described for Example 49 was followed using 1.17 g (1.0 mmol) of supported diol SD12, 884 mg (4.0 mmol) of ClPPh$_2$, 1.7 ml (10 mmol) of DIEA and 10 ml of toluene.

IR (KBr): 1741 cm$^{-1}$ (vs) Elemental Analysis: C% 85.45, H% 6.74, P% 1.14

Example 62

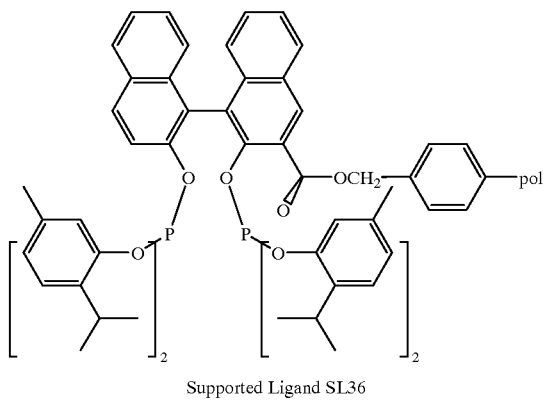

Supported Ligand SL36

This product was synthesized according to the same procedure as that for Example 49 was from 2.35 g (2.0 mmol) of the resin supported diol SD12, 2.91 g (8.0 mmol) of bis(2-isopropyl-5-methylphenyl)phosphorochloridite, 3.4 ml (10 mmol) of DIEA and 20 ml of toluene.

IR (KBr): 1741 cm$^{-1}$ (vs), 1684 cm$^{-1}$ (w) Elemental Analysis: C% 84.62, H% 6.92, P% 0.79

Example 63

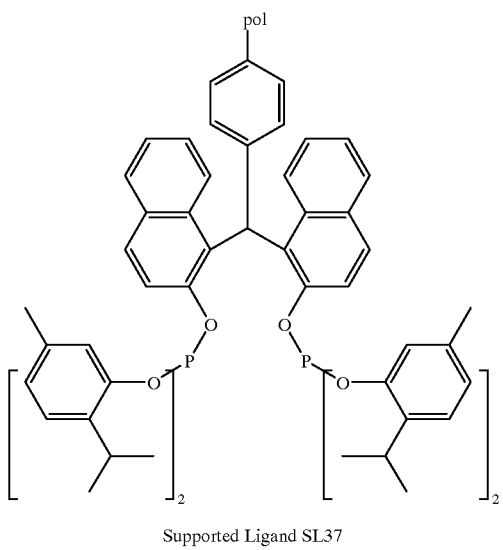

Supported Ligand SL37

The same procedure described for Example 49 was followed using 2.17 g (2.0 mmol) of supported diol SD13, 2.91 g (8.0 mmol) of bis(2-isopropyl-5-methylphenyl) phosphorochloridite, 3.4 ml (10 mmol) of DIEA and 10 ml of toluene.

Elemental Analysis: C% 90.40, H% 7.26, P% 0.61

Example 64

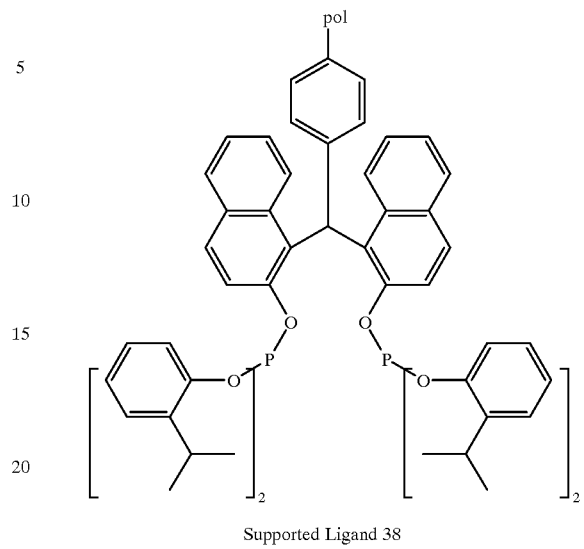

Supported Ligand 38

The same procedure described for Example 49 was followed using 2.17 g (2.0 mmol) of the resin SD13, 2.69 g (8.0 mmol) of bis(2-isopropylphenyl)phosphorochloridite, 3.4 ml (10 mmol) of DIEA and 10 ml of toluene.

Elemental Analysis: C% 90.10, H% 7.15, P% 0.48

Example 65

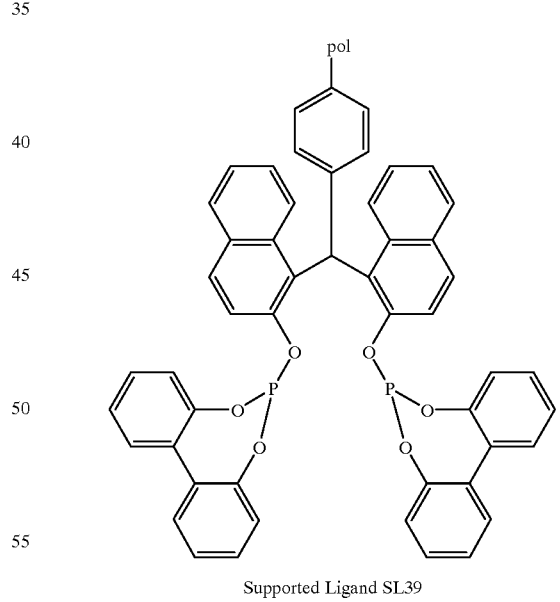

Supported Ligand SL39

The ligand was prepared according to the procedure described for Example 49 from 2.17 g (2.0 mmol) of resin SD13, 2 g of 1,1'-biphenyl-2,2'-diylphosphorochloridite (50 wt % solution in toluene, 8.0 mmol), 3.4 ml (10 mmol) of DIEA, and 20 ml of toluene.

Elemental Analysis: C% 90.28, H% 6.97, P% 0.54

Example 66

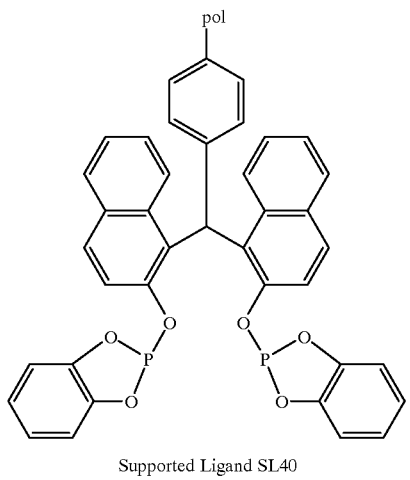

Supported Ligand SL40

The same procedure described for Example 49 was followed using 1.09 g (1.0 mmol) of resin SD13, 0.7 g (4.0 mmol) of 1,2-phenylenephosphorochloridite, 1.7 ml (10 mmol) of DIEA, and 10 ml of toluene.

Elemental Analysis: C% 89.82, H% 6.35, P% 1.19

Example 67

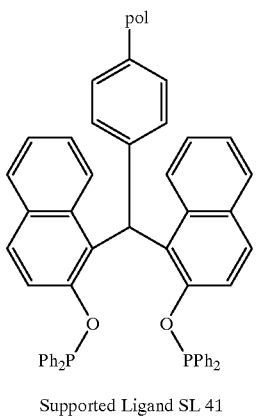

Supported Ligand SL 41

This product was obtained according to the same procedure described for Example 49 using 2.17 g (2.0 mmol) of resin SD13, 1.77 g (8.0 mmol) of PPh$_2$Cl, 3.4 ml (10 mmol) of DIEA, and 10 ml of toluene.

Elemental Analysis: C% 89.90, H% 7.46, P% 0.81

Example 68

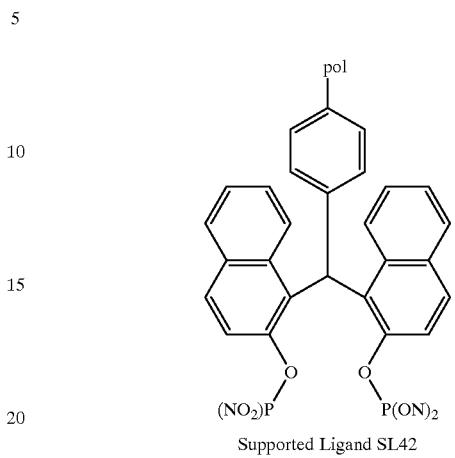

Supported Ligand SL42

N = 1-naphthyl

The same procedure described for Example 49 was followed using 2.17 g (2.0 mmol) of resin SD13, 2.82 g (8.0 mmol) of bis(1-naphthyl)phosphorochloridite, 3.4 ml (10 mmol) of DIEA, and 20 ml of toluene.

Elemental Analysis: C% 90.34, H% 7.38, P% 0.43

Example 69

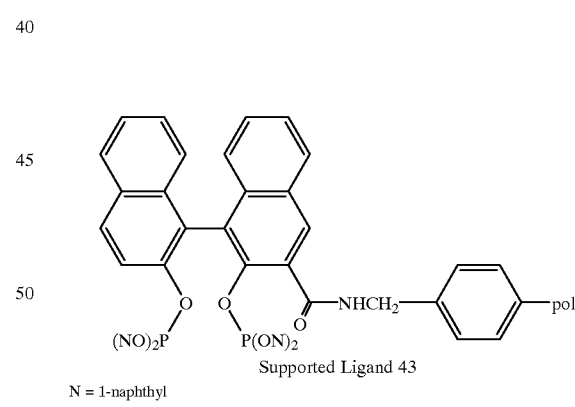

Supported Ligand 43

N = 1-naphthyl

The same procedure described for Example 49 was followed using 1.79 g (1.35 mmol) of supported diol resin SD10, 1.9 g (5.4 mmol) of bis(1-naphthyl)phosphorochloridite, 2.3 ml (10 mmol) of DIEA, and 15 ml of toluene.

IR (KBr): NH at 3436 cm$^{-1}$ (m), amide at 1668 cm$^{-1}$ (s)
Elemental Analysis: C% 83.99, H% 6.65, N% 1.22, P% 1.60

Example 70

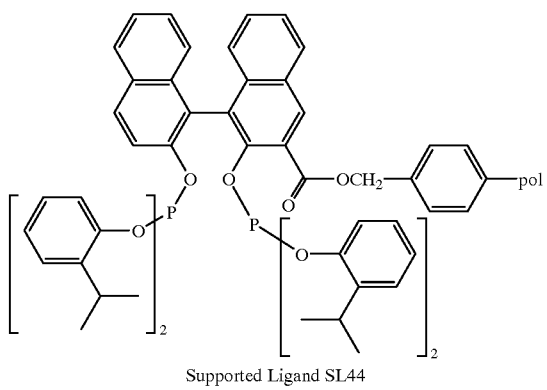

Supported Ligand SL44

The same procedure described for Example 49 was followed using 2.35 g (2.0 mmol) of the supported diol resin SD12, 2.69 g (8.0 mmol) of bis(2-isopropylphenyl)phosphorochloridite, 3.4 ml (10 mmol) of DIEA, and 20 ml of toluene.

IR (KBr): 1738 cm$^{-1}$ (s), 1676 cm$^{-1}$ (s) Elemental Analysis: C% 83.78, H% 6.49, P% 1.00

Example 71

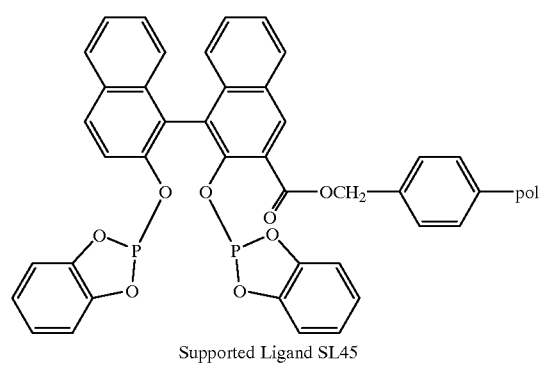

Supported Ligand SL45

The same procedure described for Example 49 was followed using 2.35 g (2.0 mmol) of resin SD12, 2.69 g (8.0 mmol) of 1,2-phenylenephosphorochloridite, 3.4 ml (10 mmol) of DIEA and 20 ml of toluene.

IR (KBr): 1739 cm$^{-1}$ (s), 1656 cm$^{-1}$ (s) Elemental Analysis: C% 83.00, H% 6.26, P% 1.70

Example 72

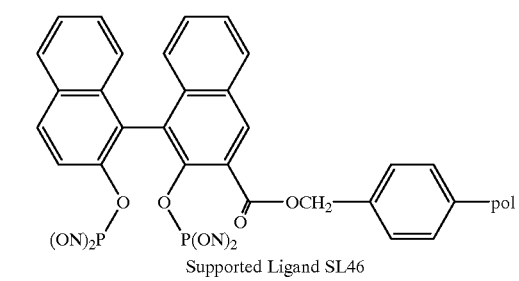

Supported Ligand SL46

N = 1-naphthyl

The same procedure described for E90113-16 was followed using 2.35 g (2.0 mmol) of resin SD12, 2.82 g (8.0 mmol) of bis(1-naphthyl)phosphorochloridite, 3.4 ml (10 mmol) of DIEA, and 20 ml of toluene.

IR (KBr): 1739 cm$^{-1}$ (vs), 1681 cm$^{-1}$ (m) Elemental Analysis: C% 84.38, H% 6.94, P% 1.25

Example 73

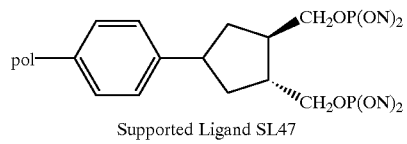

Supported Ligand SL47

N = 1-naphthyl

Following the same procedure as that described in Example 28, 1.0 g of supported diol SD4 was treated with bis(1-naphthyl)phosphorochloridite in pyridine. After ca. 3 days at room temperature the product was filtered and washed with CH$_2$Cl$_2$ and THF before vacuum drying.

Example 74

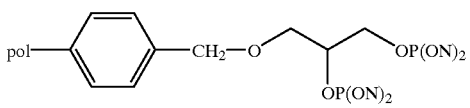

Supported Ligand SL48

N = 1-naphthyl

This supported bis(phosphite) was prepared following the same procedure described in Example 36 using bis(1-naphthyl)phosphorochloridite and supported diol SD6.

Elemental Analysis: C% 85.81, 85.99; H% 7.16; 7.39; P% 0.96

Example 75

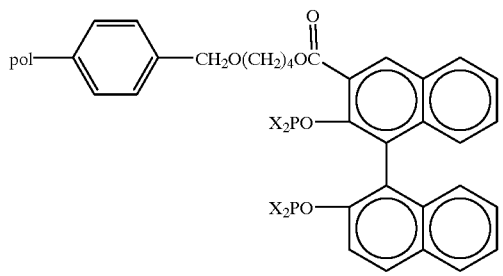

Suppported Ligand SL49

X = 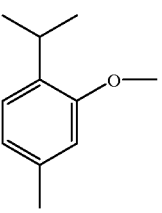

This supported bis(phosphite was prepared from supported diol SD8 following the same general procedure described in Example 43-1 using bis(2-isopropyl-5-methylphenyl)phosphorochloridite.

Elemental Analysis: C% 85.79, 85.55; H% 7.56; 7.48; P% 1.44

Example 76

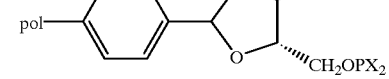

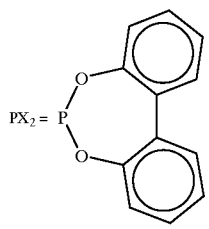

Supported Ligand SL50

This supported bis(phosphite) was prepared following the same procedure described in Example 36 using supported diol SD6 and 1,1'-biphenyl-2,2'-diylphosphorochloridite.

Example 77

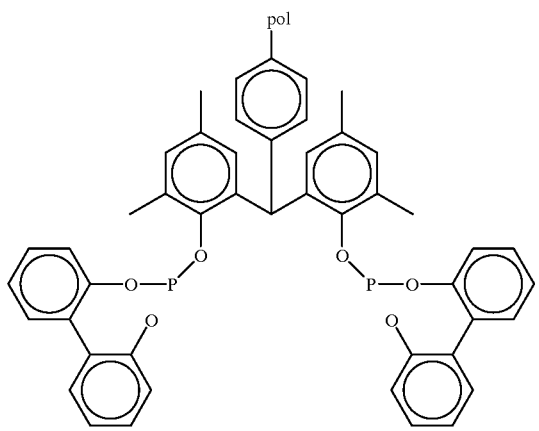

Supported Ligand SL51

This ligand was prepared according to the procedure described for Example 49 using 1.5 g (3.15 mmol) of supported diol SD14, 6.3 g (50% weight in toluene, 12.6 mmol) of 1,1'-biphenyl-2,2'-diylphosphorochloridite, 5.5 ml of DIEA and 15 ml of anhydrous toluene.

Elemental Analysis: C% 85.33, H% 7.11, P% 1.94

Example 78

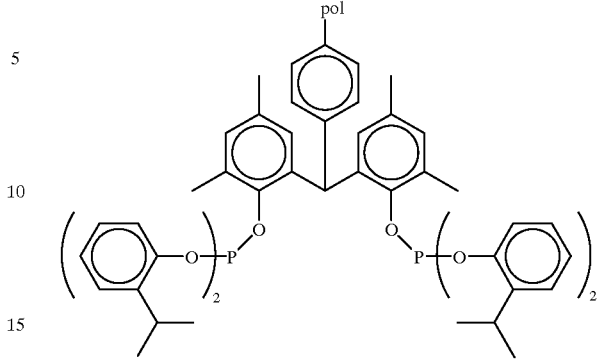

Supported Ligand SL52

This supported ligand was prepared according to the procedure described for Example 49 using 1.5 g (3.15 mmol) of supported diol SD14, 4.2 g (12.6 mmol) of bis(2-isopropylphenyl)phosphorochloridite, 5.5 ml of DIEA, and 15 ml of anhydrous toluene.

Elemental Analysis: C% 85.80, H% 7.67, P% 2.56

Example 79

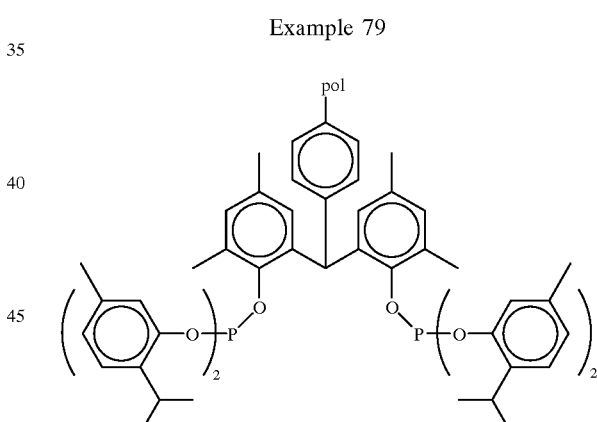

Supported Ligand SL53

This supported ligand was prepared according to the procedure described in Example 49 using 1.5 g (3.15 mmol) of resin SD14, 4.6 g (12.6 mmol) of bis(2-isopropyl-5-methylphenyl)phosphorochloridite, 5.5 ml of DIEA, and 15 ml of anhydrous toluene.

Elemental Analysis: C% 85.04, H% 7.80, P% 2.06

Example 80

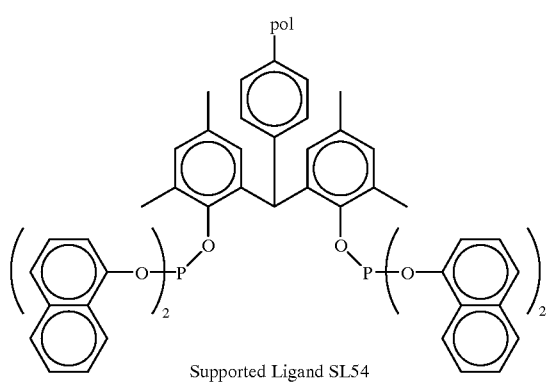

Supported Ligand SL54

This ligand was prepared according to the procedure described in Example 49 using 1.5 g (3.15 mmol) of resin SD14, 4.4 g (12.6 mmol) of bis(1-naphthyl) phosphorochloridite, 5.5 ml of DIEA and 15 ml of anhydrous toluene.

Elemental Analysis: C% 85.94, H% 7.25, P% 1.91

Example 81

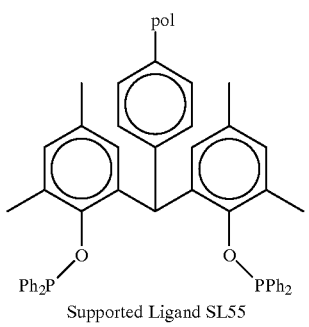

Supported Ligand SL55

This supported ligand was prepared according to the procedure described in Example 49 using 1.5 g (3.15 mmol) of resin SD14, 2.8 g (12.6 mmol) of ClPPh$_2$, 5.5 ml of DIEA and 15 ml of anhydrous toluene.

Elemental Analysis: C% 87.65, H% 7.57, P% 2.17

Example 82

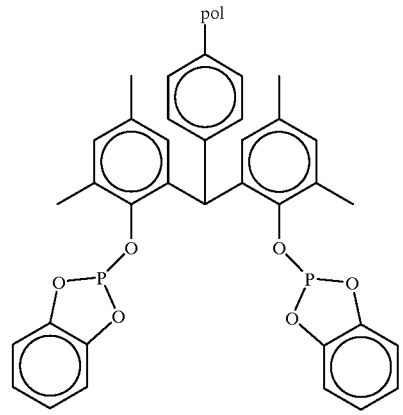

Supported Ligand SL56

This supported ligand was prepared according to the procedure described in Example 49 using 1.5 g (3.15 mmol) of supported diol SD14, 2.2 g (12.6 mmol) of 1,2-phenylenephosphorochloridite, 5.5 ml of DIEA, and 15 ml of anhydrous toluene.

Elemental Analysis: C% 84.16, H% 7.24, P% 2.41

Example 83

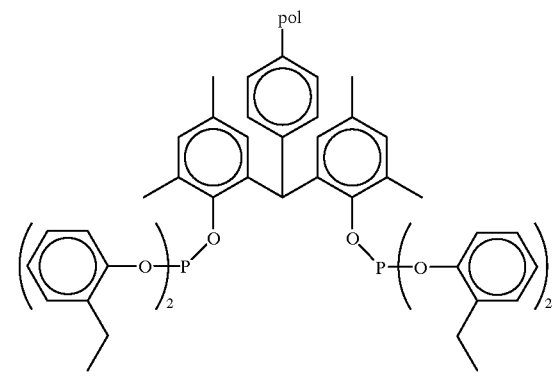

Supported Ligand SL57

This ligand was prepared according to the procedure described in Example 49 using 1.5 g (3.15 mmol) of the resin, 3.88 g (12.6 mmol) of bis(2-ethylphenyl) phosphorochloridite, 5.5 ml of DIEA and 15 ml of anhydrous toluene.

Elemental Analysis: C% 84.45, H% 7.09, P% 3.09

Example 84

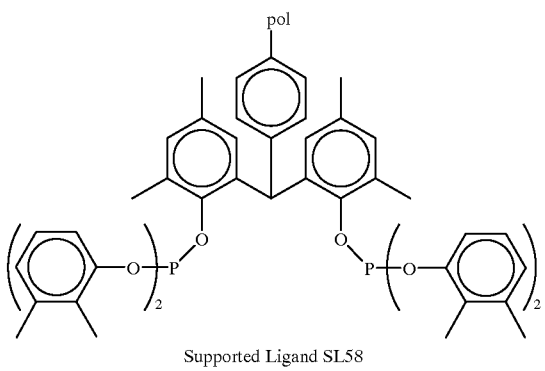

Supported Ligand SL58

This ligand was prepared according to the procedure described in Example 49 using 1.5 g (3.15 mmol) of the supported diol SD14, 3.88 g (12.6 mmol) of bis(2,3-dimethylphenyl)phosphorochloridite, 5.5 ml of DIEA, and 15 ml of anhydrous toluene.
Elemental Analysis: C% 84.97, H% 7.16, P% 2.98

Example 85

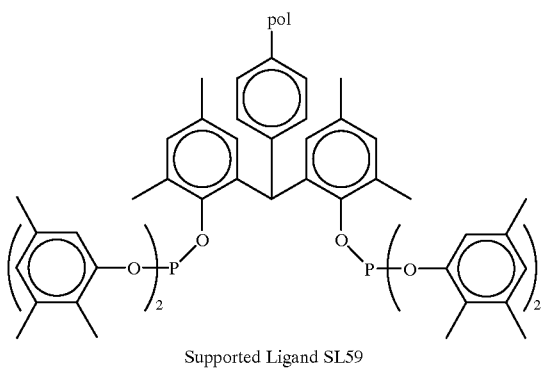

Supported Ligand SL59

This ligand was prepared according to the procedure described in Example 49 using 1.5 g (3.15 mmol) of the resin SD14, 4.23 g (12.6 mmol) of bis(2,3,5-trimethylphenyl)phosphorochloridite, 5.5 ml of DIEA, and 15 ml of anhydrous toluene.
Elemental Analysis: C % 84.65, H % 7.62, P % 2.70

Example 86

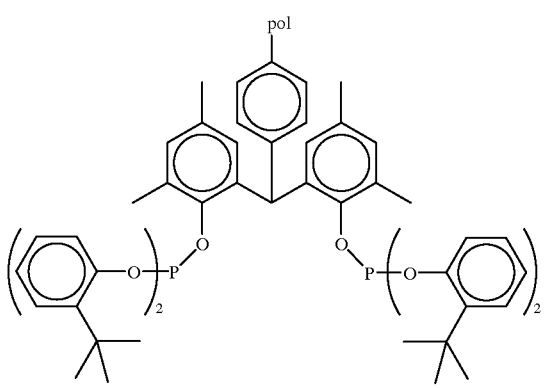

Supported Ligand SL60

This ligand was prepared according to the procedure described in Example 49 using 1.5 g (3.15 mmol) of the resin SD14, 4.60 g (12.6 mmol) of bis(2-tertbutylphenyl)phosphorochloridite, 5.5 ml of DIEA and 15 ml of anhydrous toluene.

Elemental Analysis: C % 85.83, H % 7.68, P % 2.40

Example 87

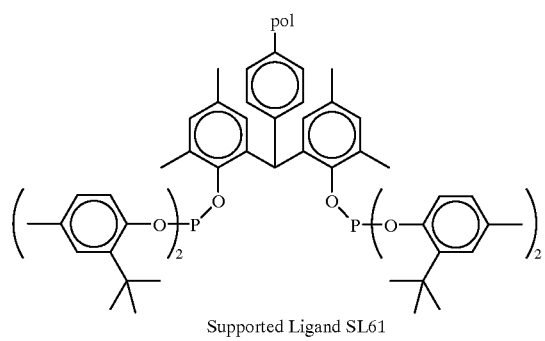

Supported Ligand SL61

This ligand was prepared according to the procedure described in Example 49 using 1.5 g (3.15 mmol) of the resin SD14, 4.95 g (12.6 mmol) of the corresponding bis(2-tertbutyl-4-methylphenyl)phosphorochloridite, 5.5 ml of DIEA and 15 ml of anhydrous toluene.

Elemental Analysis: C % 86.19, H % 7.80, P % 2.19

Example 88

The following is a general procedure for the preparation of supported nickel catalysts using the supported ligands described in previous examples. Information in Table 2 shows the generality of this procedure.

The appropriate supported ligand (0.5–1.0 g, ca. 0.5 mmol) is suspended in 15 mL of toluene in a sintered glass filter. A slight molar excess of $Ni(COD)_2$ is added and the mixture stirred with a spatula, usually for less than 1 min. The supernatant was then removed by suction filtration, washed with toluene (3×), THF (3×), and pentane (3×), before drying under vacuum. This yielded the supported catalyst, useful for olefin hydrocyanation. The product was further characterized by conversion to the supported nickel carbonyl complex by treatment of a toluene slurry of the supported Ni(COD) catalyst with CO.

TABLE 2

Supported Ni(COD) Catalysts Prepared

| Example | Supported Ligand Used | Supported Catalyst ID | Ni-CO Infrared |
|---|---|---|---|
| 88-1 | SL23 | SC25 | 2079w, 2045m, 1992s |
| 88-2 | SL24 | SC26 | 2078w, 2043m, 1991s |
| 88-3 | SL25 | SC27 | 2084w, 2045m, 1995s |
| 88-4 | SL26 | SC28 | 2062w, 2012m, 1959s |
| 88-5 | SL27 | SC29 | 2060m, 2010s |
| 88-6 | SL28 | SC30 | 2049m, 1997s |
| 88-7 | SL29 | SC31 | 2019m, 1964s |
| 88-8 | SL30 | SC32 | 2041m, 1990s |
| 88-9 | SL31 | SC33 | 2085m, 2012s |
| 88-10 | SL32 | SC34 | 2086w, 2047m, 2007s |
| 88-11 | SL33 | SC35 | 2062m, 2013s |
| 88-12 | SL34 | SC35 | 2047m, 1994s |
| 88-13 | SL35 | SC37 | 2073m, 1997s, 1964s |
| 88-14 | SL36 | SC38 | 2082m, 2054m, 2008s, 1984s |
| 88-15 | SL37 | SC39 | 2082m, 2013s |
| 88-16 | SL39 | SC40 | |
| 88-17 | SL40 | SC41 | 2059m, 2009s |
| 88-18 | SL41 | SC42 | 2072w, 2010m, 1961s |
| 88-19 | SL43 | SC43 | 2048m, 1998s |
| 88-20 | SL44 | SC44 | 2085m, 2065m, 2010s |
| 88-21 | SL45 | SC45 | |
| 88-22 | SL47 | SC46 | 2086m, 2043m, 1991s |
| 88-23 | SL49 | SC48 | 2080m, 2036m, 2003s |
| 88-24 | SL50 | SC49 | 2083w, 2041m, 2017w, 1990s |
| 88-25 | SL51 | SC50 | 2084vw, 2042s, 1989vs |
| 88-26 | SL52 | SC51 | 2083vw, 2039s, 2013m, 1986s |
| 88-27 | SL53 | SC52 | 2082m, 2040m, 2009s, 1981s |
| 88-28 | SL54 | SC53 | 2083m, 2041m, 2022s, 1988s |
| 88-29 | SL55 | SC54 | 2073m, 2012s, 1958s |
| 88-30 | SL56 | SC55 | 2058m, 2010s |
| 88-31 | SL42 | SC56 | |
| 88-31 | SL46 | SC57 | |

Example 89

Supported ligand SL33 (0.489 g) was placed in 5 mL of toluene. To this solution was added 0.268 g of Ni(oTTP)$_3$ (oTTP=ortho-tritolylphosphite). The mixture was stirred occasionally with a spatula and then filtered. The resulting orange, nickel supported catalyst SC58 was washed with toluene (3×) and CH$_2$Cl$_2$(3×) before vacuum drying.

A 50 mg aliquot of this sample was placed in 5 mL of toluene and then CO was bubbled through the solution at 1 atm. The orange color immediately dissipated to give a beige product. The resin was filtered, washed with solvent (toluene, CH$_2$Cl$_2$) and dried in vacuum. Infrared analysis showed a single Ni—CO absorption at 2011 cm$^{-1}$.

Example 90

Butadiene Hydrocyanation with Supported Nickel Catalysts

The resin supported ligand and nickel were charged as either the Ni(COD) loaded material, prepared as described above, or by separate addition of Ni(COD)$_2$ and ligand. The amount of supported ligand charged was targeted at 5.4 micromoles and a 1:1 ratio of chelate ligand to nickel, except where noted. 5 mL of solvent (toluene or tetrahydrofuran) was used as the reaction solvent, and the experiments were conducted at 80° C. The reaction mixtures are made to a target HCN/Ni ratio of 500 and to a target HCN/BD ratio of 0.89. The resulting concentrations of HCN and BD are 2.3 M and 2.64 M, respectively. Valeronitrile acts as the internal standard. "Total PN, %" represents the sum of %3PN and %2M3. Aliquots were removed at the indicated reaction times for gas chromatographic analysis. As used below in Table 3, pTTP=paratritolylphosphite.

TABLE 3

Butadiene Hydrocyanation

| Example | Supported Ligand/Catalyst | Time, hours | Total PN, % | 3PN/2M3 Ratio |
|---|---|---|---|---|
| Comparative Example | pTTP + Ni(COD)$_2$ | 1.5 | 10.7 | 0.51 |
| | | 3.25 | 16.4 | 0.49 |
| 90-1 | SL1 | 2.0 | 23.0 | 1.45 |
| | | 3.0 | 27.4 | 1.29 |

TABLE 3-continued

Butadiene Hydrocyanation

| Example | Supported Ligand/Catalyst | Time, hours | Total PN, % | 3PN/2M3 Ratio |
|---|---|---|---|---|
| 90-2 | SL3-1 | 2.0 | 12.5 | 0.81 |
|  |  | 3.0 | 13.4 | 0.77 |
| 90-3 | SL3-2 | 2.0 | 24.2 | 0.73 |
|  |  | 3.0 | 40.1 | 0.77 |
| 90-4 | SL2 | 2.0 | 0.1 | — |
|  |  | 3.0 | 2.6 | 0.88 |
| 90-5A | SL3/SC4 | 2.0 | 33.7 | 0.71 |
|  |  | 3.0 | 40.3 | 0.67 |
| 90-5B | SL3/SC4 repeat with | 2.0 | 2.2 | 0.83 |
|  | half the Ni loading | 3.0 | 16.3 | 0.75 |
| 90-6 | SL4 | 1.5 | 0.8 | 0.65 |
| 90-7 | SL50 | 1.5 | 3.9 | 0.75 |
|  |  | 3.0 | 12.1 | 0.73 |
| 90-8 | SL7 | 1.5 | 0.8 | 0.9 |
|  |  | 2.8 | 1.2 | 0.87 |
| 90-9 | SL8 | 1.5 | 0.3 | 1.96 |
|  |  | 2.8 | 0.6 | 2.02 |
| 90-10 | SL9 | 1.5 | 0.3 | 1.6 |
|  |  | 3.0 | 0.3 | 1.53 |
| 90-11 | SL10 | 1.5 | 0.2 | 2.63 |
|  |  | 3.0 | 0.2 | 2.63 |
| 90-12 | SL12 | 3.0 | 22.4 | 1.72 |
| 90-13 | SL13 | 1.5 | 2.3 | 0.71 |
|  |  | 3.0 | 3.7 | 0.69 |
| 90-14 | SL15 | 1.5 | 1.3 | 0.57 |
|  |  | 3.0 | 1.3 | 0.57 |
| 90-15 | SL15 | 1.5 | 1.7 | 0.57 |
|  |  | 3.0 | 2.1 | 0.61 |
| 90-16 | SL14 | 1.5 | 3.9 | 0.73 |
|  |  | 3.0 | 12.0 | 0.71 |
| 90-17 | SL14 | 1.5 | 0.4 | 1.26 |
|  |  | 3.0 | 6.0 | 0.72 |
| 90-19 | SL16 | 1.5 | 9.5 | 0.81 |
|  |  | 3.0 | 10.8 | 0.78 |
| 90-20 | SL16 | 1.5 | 9.6 | 0.79 |
|  |  | 3.0 | 18.3 | 0.78 |
| 90-21 | SL18 | 1.5 | 2.0 | 0.90 |
|  |  | 3.0 | 3.3 | 0.87 |
| 90-22 | SL17 | 1.5 | 1.3 | 0.84 |
|  |  | 3.0 | 2.2 | 0.77 |
| 90-23 | SL19 | 1.5 | 0.6 | 0.81 |
|  |  | 3.0 | 0.9 | 0.67 |
| 90-24 | SL20 | 1.5 | 0.0 | — |
|  |  | 3.0 | 0.4 | 0.73 |
| 90-25 | SL21 | 1.5 | 1.7 | 0.86 |
|  |  | 3.0 | 3.0 | 0.79 |
| 90-26 | SL22 | 1.5 | 0.0 | — |
|  |  | 3.0 | 0.6 | 0.79 |
| 90-27 | SL5 | 1.5 | 52.7 | 1.10 |
| 90-28 | SL47/SC | 1.5 | 1.1 | 0.83 |
|  |  | 3.0 | 0.7 | 1.04 |
| 90-29 | SL48 | 1.5 | 2.3 | 1.41 |
|  |  | 3.0 | 2.5 | 1.44 |
| 90-30 | SL49 | 1.5 | 2.7 | 1.02 |
|  |  | 3.0 | 5.1 | 1.02 |
| 90-31 | SL23/SC25 | 1.58 | 13.3 | 0.94 |
|  |  | 3.0 | 11.7 | 0.97 |
| 90-32A | SL26/SC28 | 1.58 | 14.7 | 0.39 |
|  |  | 3.0 | 10.7 | 0.40 |
| 90-32B | SL26/SC28 | 1.5 | 5.3 | 0.40 |
|  |  | 2.0 | 9.3 | 0.41 |
| 90-33A | SL27/SC29 | 1.58 | 7.2 | 3.6 |
|  |  | 3.0 | 3.7 | 3.5 |
| 90-33B | SL27/SC29 | 1.5 | 2.9 | 3.42 |
|  |  | 3.0 | 2.0 | 3.29 |
| 90-34 | SL24/SC26 | 1.58 | 1.6 | 0.47 |
|  |  | 3.0 | 9.3 | 0.49 |
| 90-35A | SL25/SC27 | 1.58 | 15.7 | 0.65 |
|  |  | 3.0 | 12.3 | 0.63 |
| 90-35B | SL25/SC27 | 1.5 | 10.1 | 0.59 |
|  |  | 3.0 | 11.9 | 0.58 |
| 90-36A | SL32/SC34 | 1.67 | 20.5 | 1.09 |
|  |  | 3.0 | 23.1 | 1.09 |
| 90-36B | SL32/SC34 | 1.5 | 5.5 | 0.85 |

TABLE 3-continued

Butadiene Hydrocyanation

| Example | Supported Ligand/Catalyst | Time, hours | Total PN, % | 3PN/2M3 Ratio |
|---|---|---|---|---|
| | | 3.0 | 6.3 | 0.82 |
| 90-37A | SL31/SC33 | 1.67 | 0.4 | 0.83 |
| | | 3.0 | 0.4 | 0.75 |
| 90-37B | SL31/SC33 | 1.5 | 0.5 | 0.63 |
| | | 3.0 | 0.5 | 0.68 |
| 90-38A | SL30/SC32 | 1.67 | 36.9 | 1.42 |
| 90-38B | SL30/SC32 | 1.5 | 8.2 | 0.44 |
| | | 3.0 | 6.4 | 0.44 |
| 90-38C | SL30/SC32 | 1.5 | 6.4 | 0.46 |
| | | 3.0 | 7.8 | 0.45 |
| 90-38D | SL30/SC32 | 1.5 | 5.1 | 0.38 |
| | | 3.0 | 5.9 | 0.38 |
| 90-38E | SL30/SC32 | 1.5 | 6.9 | 0.44 |
| | | 3.0 | 7.1 | 0.44 |
| 90-39 | SL29/SC31 | 1.67 | 0.5 | 0.63 |
| | | 3.0 | 3.8 | 0.84 |
| 90-40A | SL28/SC30 | 1.67 | 5.2 | 0.84 |
| | | 3.0 | 2.5 | 0.39 |
| 90-40B | SL28/SC30 | 1.5 | 15.0 | 0.74 |
| | | 3.0 | 18.6 | 0.71 |
| 90-41A | SL37/SC39 | 1.5 | 1.8 | 0.55 |
| | | 3.0 | 2.7 | 0.57 |
| 90-41B | SL37/SC39 | 1.5 | 3.1 | 0.54 |
| | | 3.0 | 4.0 | 0.53 |
| 90-42A | SL41/SC42 | 1.5 | 3.7 | 0.44 |
| | | 3.0 | 4.3 | 0.46 |
| 90-42B | SL41/SC42 | 1.5 | 4.0 | 0.44 |
| | | 3.0 | 3.4 | 0.46 |
| 90-43A | SL34/SC36 | 1.5 | 20.4 | 0.69 |
| | | 3.0 | 25.1 | 0.65 |
| 90-43B | SL34/SC36 | 1.5 | 28.7 | 0.69 |
| | | 3.0 | 28.2 | 0.64 |
| 90-43C | SL34/SC36 | 1.5 | 16.8 | 0.70 |
| | | 3.0 | 27.0 | 0.63 |
| 90-44A | SL35/SC37 | 1.5 | 7.7 | 0.32 |
| | | 3.0 | 8.5 | 0.32 |
| 90-44B | SL35/SC37 | 1.5 | 9.2 | 0.31 |
| | | 3.0 | 8.7 | 0.31 |
| 90-45 | SL43/SC43 | 1.5 | 17.9 | 0.95 |
| | | 3.0 | 26.5 | 0.89 |
| 90-46 | SL44/SC44 | 1.5 | 2.5 | 0.44 |
| | | 3.0 | 2.9 | 0.44 |
| 90-47 | SL36/SC38 | 1.5 | 7.1 | 0.37 |
| | | 3.0 | 8.7 | 0.36 |
| 90-48 | SL51/SC50 | 1.5 | 29.8 | 1.60 |
| | | 3.0 | 30.7 | 1.61 |
| 90-49 | SL52/SC51 | 1.5 | 15.8 | 0.64 |
| | | 3.0 | 18.8 | 0.65 |
| 90-50 | SL53/SC52 | 1.5 | 16.7 | 0.53 |
| | | 3.0 | 14.5 | 0.59 |
| 90-51 | SL54/SC52 | 1.5 | 21.2 | 1.06 |
| | | 3.0 | 22.9 | 1.09 |
| 90-52 | SL55/SC54 | 1.5 | 46.7 | 0.43 |
| | | 3.0 | 46.3 | 0.44 |
| 90-53 | SL56/SC55 | 1.5 | 0.9 | 1.16 |
| | | 3.0 | 1.0 | 1.24 |

Example 91

Butadiene Hydrocyanation—Vapor Phase

An empty 0.24 inch (0.64 cm) diameter, 15 inch (37.5) long stainless steel tubular reactor was placed in a nitrogen filled glove box. A plug of glass wool was placed in the bottom end of the reactor, followed by the amount and type of supported catalyst as shown in Table 4. A thermocouple was inserted into the top of the reactor. Both ends of the reactor were sealed with metal fittings, and the reactor was removed from the glove box and connected to stainless steel reactor feed lines purged with nitrogen. The feed streams consisted of approximately 2.2 vol % gaseous HCN in nitrogen and gaseous butadiene (BD). The reactor was heated in a split tube furnace to 145° C. Gaseous effluent from the reactor passed through a heated sampling valve which permitted periodic on-line gas chromatographic analyses of products. GC analyses were done on a 30 m DB-23 capillary column of a 0.32 mm internal diameter, supplied by J&W Scientific, Folsom, Calif. The stationary phase was cyanopropyl (50%) methylpolysiloxane. Table 4 shows the specific reaction conditions and summarizes the results. Percent selectivity to (3PN+4PN+2M3BN) was determined as (GC area % for 3PN+4PN+2M3BN)/GC are % for PNs)×100.

TABLE 4

Butadiene Hydrocyanation - Vapor Phase
(All experiments conducted at 145° C.)

| Example | Supported Catalyst | Feed mmol/hour | Elapsed Time, h | GC Area % PNs | DNs | Selectivity % | $\frac{3PN}{2M3}$ Ratio |
|---|---|---|---|---|---|---|---|
| 91-1 | SCI 0.87 g | BD 1.13 HCN 0.28 | 0.5 | 8.2 | | 100 | 1.4 |
| | | | 3.5 | 9.4 | | 100 | 4.5 |
| | | | 6.5 | 9.4 | | 100 | 4.0 |
| | | | 9.5 | 9.8 | | 100 | 1.8 |
| | | | 12.5 | 10.4 | | 100 | 0.9 |
| | | | 15.5 | 4.2 | | 100 | 0.8 |
| | | | 17.5 | 3.1 | | 100 | 0.8 |
| 91-2 | SC4 0.96 g | BD 1.13 HCN 0.28 | 2.75 | 11.5 | | 88.7 | 12.5 |
| | | | 8.75 | 11.1 | 0.22 | 96.3 | 10.4 |
| | | | 13.75 | 10.8 | 0.23 | 100 | 7.6 |
| | | | 19.75 | 10.9 | 0.31 | 100 | 4.2 |
| | | | 25.75 | 10.2 | 0.35 | 100 | 2.9 |
| | | | 31.75 | 10.0 | 0.33 | 100 | 2.4 |
| | | | 37.75 | 10.0 | 0.24 | 100 | 2.1 |
| | | | 43.75 | 9.7 | 0.28 | 100 | 1.9 |
| | | | 49.75 | 9.3 | 0.28 | 100 | 1.8 |
| | | | 55.75 | 9.3 | 0.26 | 100 | 1.7 |
| | | | 61.75 | 9.0 | 0.23 | 100 | 1.6 |
| | | | 67.75 | 8.6 | 0.26 | 100 | 1.5 |
| 91-3 | SC5 0.89 g | BD 1.13 HCN 0.28 | 1 | 10.8 | | 79.4 | 13.0 |
| | | | 3 | 12.6 | | 86.9 | 11.8 |
| | | | 9 | 12.1 | | 95.0 | 11.1 |
| | | | 15 | 12.5 | | 95.0 | 9.3 |
| | | | 21 | 13.8 | | 95.1 | 1.7 |
| | | | 27 | 13.4 | | 95.0 | 1.5 |
| | | | 33 | 13.3 | 0.24 | 94.8 | 1.3 |
| | | | 39 | 12.5 | | 94.8 | 1.2 |
| | | | 45 | 11.7 | | 94.9 | 1.2 |
| | | | 51 | 10.4 | | 94.7 | 1.1 |

Example 92

3-Pentenenitrile Hydrocyanation with Supported Nickel Catalysts

The resin supported ligand and nickel were charged as the preformed nickel-loaded, supported catalyst. The amount of supported ligand charged was 8.5 micromoles, and a 1:1 ratio of ligand to nickel was used. $ZnCl_2$ was added as a promoter, using a ratio 1:1 $ZnCl_2$:Ni. To the catalyst and promoter was added 5 mL of a 40 mole % solution in HCN in trans-3-pentenenitrile. The sample was analyzed by gas chromatography after 24 h at 25° C. In the Table below, % HCN conversion refers to the amount of HCN converted to hydrocyanation products, and % ADN distribution refers to the per cent amount of ADN relative to all isomeric dinitrile products (% ADN Distribution=100×ADN/(ADN+MGN+ESN)). ADN refers to adiponitrile, MGN refers to methylglutaronitrile, and ESN refers to ethylsuccinonitrile. A comparative example using a commercial homogeneous catalyst based on pTTP (pTTP is para-tritolylphosphite) and nickel (0) is provided in the Table below, showing that the supported catalysts perform better than current commercial soluble catalysts.

TABLE 5

| Example | Ligand | Catalyst | HCN Conversion (%) | ADN Distribution (%) |
|---|---|---|---|---|
| Comparative Example | pTTP | pTTP + Ni(COD)$_2$ | 5.6 | 63.3 |
| 92-1 | SL12 | SC14 | 69.3 | 66.6 |
| 92-2 | SL41 | SC42 | 32.0 | 80.1 |

TABLE 5-continued

| Example | Ligand | Catalyst | HCN Conversion (%) | ADN Distribution (%) |
|---|---|---|---|---|
| 92-3 | SL28 | SC30 | 23.5 | 67.9 |
| 92-4 | SL43 | SC43 | 20.8 | 63.5 |
| 92-5 | SL25 | SC27 | 15.5 | 80.1 |
| 92-6 | SL35 | SC37 | 14.0 | 74.7 |
| 92-7 | SL32 | SC34 | 13.5 | 86.9 |
| 92-8 | SL32 | SC34 | 5.0 | 80.1 |
| 92-9 | SL26 | SC28 | 12.8 | 75.7 |
| 92-10 | SL37 | SC39 | 12.5 | 87.9 |
| 92-11 | SL27 | SC29 | 11.3 | 69.2 |
| 92-12 | SL44 | SC44 | 10.0 | 87.0 |
| 92-13 | SL30 | SC32 | 8.0 | 85.4 |
| 92-14 | SL26 | SC32 | 8.3 | 87.2 |
| 92-15 | SL51 | SC50 | 83.5 | 59.0 |
| 92-16 | SL40 | SC41 | 73.5 | 59.4 |
| 92-17 | SL52 | SC51 | 48.3 | 77.2 |
| 92-18 | SL45 | SC45 | 29.0 | 71.6 |
| 92-19 | SL42 | SC56 | 25.8 | 42.2 |
| 92-20 | SL39 | SC40 | 23.5 | 64.2 |
| 92-21 | SL46 | SC57 | 17.8 | 51.7 |
| 92-22 | SL53 | SC52 | 14.3 | 84.2 |
| 92-23 | SL54 | SC53 | 14.0 | 73.9 |
| 92-24 | SL55 | SC54 | 10.5 | 85.8 |
| 92-25 | SL56 | SC55 | 8.8 | 61.5 |
| 92-26 | SL33 | SC35 | 17.8 | 40.3 |
| 92-27 | SL33 | SC58 | 7.8 | 75.8 |

Example 93

Olefin Hydrogenation—General Procedure

A vial is charged with 2 mmol of olefin, the supported rhodium catalyst (0.014 mmol Rh), and 2 mL of THF. The vial is placed in a shaker tube and then treated with hydrogen at the desired temperature, pressure, and time. A 100 μL aliquot of the supernatant is removed, diluted with 500 μL THF, and analyzed by GC. The results are provided in Table 6.

Example 94

Olefin Hydrogenation—Catalyst Recycle/Metal Leaching 100 mg of the rhodium-loaded resin from Example 8 was charged to a glass pressure vessel. 1 mL of cyclooctene and 10 mL of THF were added. The vessel was pressurized with 50 psig $H_2$ and heated to 50° C., with stirring. After 2 h the pressure dropped to 25 psi. The liquid supernatant was removed with a syringe. GC analysis showed 100% conversion of the cyclooctene to cyclooctane. Analysis of the supernatant further showed 3 ppm Rh. Fresh cyclooctene (1 mL) and THF (10 mL) were added to the remaining rhodium-loaded resin remaining in the reactor and the hydrogenation process was repeated.

These results show that the resins of this invention are resistant to metal leaching and are amenable to recycle.

TABLE 7

Cyclooctene Hydrogenation/Catalyst Recycle and Metal Leaching

| Cycle # | Conversion % (2 h) | Turnovers mol COE/mol Rh | [Rh] Supernatant ppm |
|---|---|---|---|
| 1 | 100 | 416 | 3 |
| 2 | 96 | 399 | 1 |
| 3 | 70 | 291 | 1 |
| 4 | 81 | 337 | undetected |

Example 95

Hydrosilation Catalysis—General Procedure

A vial was charged with 9.5 mg of the supported rhodium catalyst SC3, corresponding to 0.18 μmole of rhodium. The

TABLE 6

Olefin Hydrogenation with Resin Supported Rhodium Complexes

| Example | Substrate | Catalyst | Pressure (psig) | Temp (° C.) | Time | Product | Conversion (GC Area %) |
|---|---|---|---|---|---|---|---|
| 93-1 | cis-cyclooctene | SC2 | 100 | 50 | 3 | cyclooctane | 100 |
| 93-2 | cis-cyclooctene | SC2 | 50 | 21 | 0.75 | cyclooctane | 11 |
| 93-3 | cis-cyclooctene | SC3 | 50 | 50 | 0.75 | cyclooctane | 21 |
| 93-4 | cis-cyclooctene | SC2 | 50 | 50 | 2 | cyclooctane | 100 |
| 93-5 | styrene | SC2 | 100 | 50 | 3 | ethylbenzene | 14 |
| 93-6 | a-methylstyrene | SC2 | 100 | 50 | 3 | isopropylbenzene | 12 |
| 93-7 | trans-PhCHC($CH_3$)($CO_2CH_3$) | SC2 | 100 | 50 | 3 | $PhCH_2CH(CH_3)(CO_2CH_3)$ | 2 |

This overall process was repeated an additional two times and the results are shown in Table 7. The final example shows that metal leaching is below the detection limits and yet catalyst activity is maintained. To the supernatant from the final cycle was added 0.725 g of norbornylene. The resulting solution was treated with 50 psi $H_2$ at 50° C. After 2 h no gas uptake was detected. GC analysis of the solution showed no hydrogenation of norbornylene to norbornane had occurred. This result shows that hydrogenation activity occurs with the rhodium-supported catalyst and can not be attributed to metal leached into solution.

vial was then charged with 12 mg (0.1 mmol) of $Et_3SiH$, 24 mg (0.2 mmol) of acetophenone, and 1 mL of toluene. The vial was then heated for the indicated time and temperature. The supernatant was then analyzed by GC, which showed a 36% conversion to $PhCH(CH_3)OSiEt_3$. The remaining examples shown in Table 8 were performed in a similar manner. The last entry in this table, Comparative Example 95-14 shows the results obtained with a known homogeneous catalyst for this reaction, $RhTPP_3Cl$ (TPP=triphenylphosphine).

TABLE 8

Hydrosilation with Resin-Supported Rhodium Catalysts

| Reference | Catalyst | Silane | Substrate | Temp ° C. | Time h | Product | Conversion GC Area % |
|---|---|---|---|---|---|---|---|
| 95-1 | SC2 | $Et_3SiH$ | acetophenone | 60 | 0.3 | ⌬—CH($CH_3$)$OSiEt_3$ | 5.2 |
| 95-2 | SC2 | " | acetophenone | 85 | 2 | ⌬—CH($CH_3$)$OSiEt_3$ | 30 |
| 95-3 | SC2 | " | 1-hexene | 85 | 2 | $CH_3(CH_2)_5SiEt_3$ | 20 |
| 95-4 | SC2 | $Me_2PhSiH$ | " | 85 | 2 | $CH_3(CH_2)_5SiMe_2Ph$ | 100 |

TABLE 8-continued

Hydrosilation with Resin-Supported Rhodium Catalysts

| Reference | Catalyst | Silane | Substrate | Temp °C. | Time h | Product | Conversion GC Area % |
|---|---|---|---|---|---|---|---|
| 95-5 | SC2 | Et₃SiH | phenylacetylene | 85 | 2 | 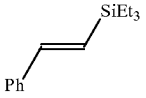 | 74 |
| 95-6 | SC3 | Et₃SiH | acetophenone | 85 | 0.25 | 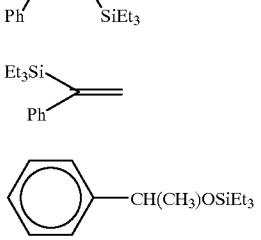 | 0 |
| 95-7 | SC3 | " | " | 85 | 2 | 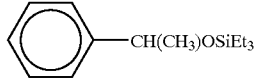 | 36 |
| 95-8 | SC3 | " | 1-hexene | 85 | 0.25 | CH₃(CH₂)₅SiEt₃ | 0 |
| 95-9 | SC3 | " | " | 85 | 2 | " | 2 |
| 95-10 | SC3 | Me₂PhSiH | " | 85 | 0.25 | CH₃(CH₂)₅SiMe₂Ph | 0.8 |
| 95-11 | SC3 | " | " | 85 | 2 | " | 88 |
| 95-12 | SC3 | " | phenylacetylene | 85 | 0.25 | 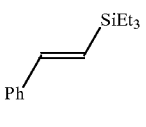 | 13 |
| 95-13 | SC3 | " | phenylacetylene | 85 | 0.25 | " | 77 |
| 95-14 (Compar. Example) | RhTPP₃Cl | Et₃SiH | acetophenone | 60 | 0.25 | 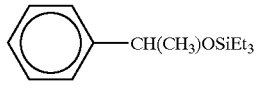 | 38 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A supported diol selected from the group consisting of the following structures:

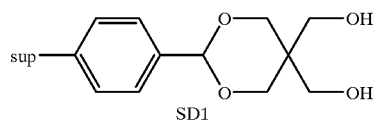

SD1

-continued

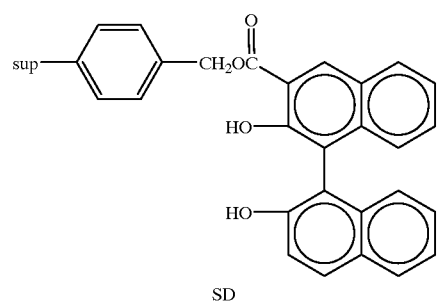

SD

-continued

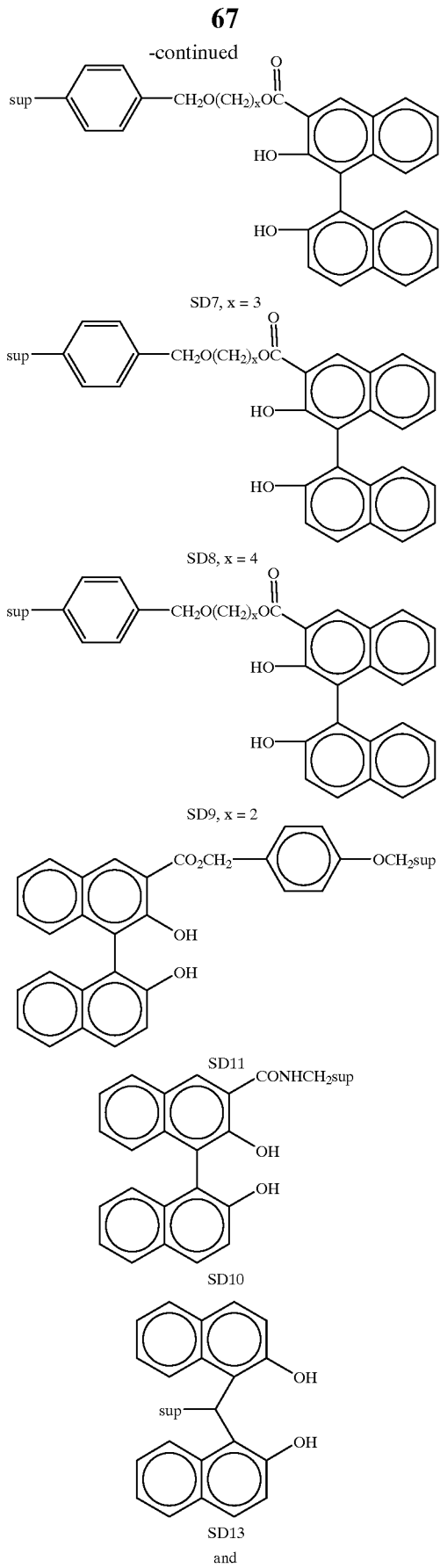

SD7, x = 3

SD8, x = 4

SD9, x = 2

SD10

SD13 and

-continued

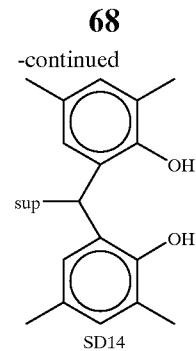

SD14 wherein x is 2, 3, or 4; and sup is a support.

2. The supported diol according to claim 1 wherein the support is an organic polymer resin.

3. The supported diol according to claim 2 wherein the organic polymer resin is a crosslinked polystyrene resin.

4. A supported bis(phosphorus) ligand according to formula (2):

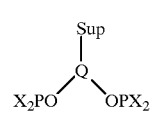 (2)

wherein:

Q is any organic fragment which binds a $OPX_2$ moiety to the support (Sup); and X is an alkoxide, aryloxide, alkyl, or aryl.

5. The ligand according to claim 4 wherein the support is an organic polymer resin.

6. The ligand according to claim 4 wherein X is aryloxide or aryl.

7. A supported catalyst composition according to formula (3):

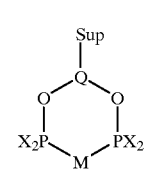 (3)

wherein:

Q is any organic fragment which binds a $OPX_2$ moiety to the support (Sup).;

X is an alkoxide, aryloxide, alkyl or aryl; and

M is a transition metal capable of carrying out catalytic transformations.

8. The supported catalyst composition of claim 7 wherein the support is an organic polymer resin.

9. The catalyst composition of claim 7 wherein X is aryloxide or aryl.

10. The catalyst composition of claim 7 wherein M is selected from the group consisting of Ni, Rh, Co, Ir, Pd, Pt, and Ru.

11. A catalytic hydrogenation or hydrosilation process utilizing the catalyst composition of claim 7.

12. A hydrocyanation process comprising reacting an acyclic, aliphatic, monoethylenically unsaturated compound in which the ethylenic double bond is not conjugated to any other olefinic group in the molecule, or a monoethylenically unsaturated compound in which the ethylenic double bond is conjugated to an organic ester group, with a source of hydrogen cyanide (HCN) in the presence of a supported catalyst composition according to formula (3):

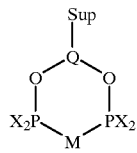
(3)

wherein:

Q is any organic fragment which binds a $OPX_2$ group to the support (Sup).;

X is an alkoxide, aryloxide, alkyl or aryl; and

M is nickel, wherein the process is run in a gas or a liquid phase.

13. The process of claim 12 wherein the support is an organic polymer resin.

14. The process of claim 12 wherein X is aryloxide or aryl.

15. The process of claim 12 wherein the reaction is run in the liquid phase.

16. A hydrocyanation process comprising reacting an acyclic aliphatic diolefinic compound with a source of hydrogen cyanide (HCN) in the presence of a supported catalyst composition according to formula (3):

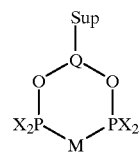
(3)

wherein:

Q is any organic fragment which binds a $OPX_2$ group to the support (Sup).;

X is an alkoxide, aryloxide, alkyl or aryl; and

M is nickel, wherein the process is run in a gas phase or a liquid phase.

17. The process of claim 16 wherein the support is an organic polymer resin.

18. The process of claim 16 wherein X is aryloxide or aryl.

19. The process of claim 16 wherein the reaction is run in the liquid phase.

20. The process of claim 16 wherein the reaction is run in the gas phase.

21. The process of claim 16 wherein the diolefinic compound is 1,3-butadiene.

22. The ligand according to claim 4 wherein the $PX_2$ group forms a ring and $X_2$ is a di(alkoxide), di(aryloxide), di(alkyl) or di(aryl).

23. The catalyst composition according to claim 7 wherein the $PX_2$ group forms a ring and $X_2$ is a di(alkoxide), di(aryloxide), di(alkyl) or di(aryl).

24. The process of claim 12 wherein the reaction is run in the gas phase.

* * * * *